US011649492B2

(12) United States Patent
Alexander et al.

(10) Patent No.: US 11,649,492 B2
(45) Date of Patent: May 16, 2023

(54) DEEP SEQUENCING PROFILING OF TUMORS

(71) Applicants: Roche Sequencing Solutions, Inc., Pleasanton, CA (US); Ventana Medical Systems, Inc., Tucson, AZ (US)

(72) Inventors: Nelson R Alexander, Marana, AZ (US); Daniel Burgess, Madison, WI (US); Heidi J Rosenbaum, Middleton, WI (US); Stacey Stanislaw, Tucson, AZ (US)

(73) Assignees: Roche Sequencing Solutions, Inc., Pleasanton, CA (US); Ventana Medical Systems, Inc., Tucson, AZ (US)

( * ) Notice: Subject to any disclaimer, the term of this patent is extended or adjusted under 35 U.S.C. 154(b) by 274 days.

(21) Appl. No.: 16/034,392

(22) Filed: Jul. 13, 2018

(65) Prior Publication Data

US 2018/0320229 A1 Nov. 8, 2018

Related U.S. Application Data

(63) Continuation of application No. PCT/US2016/060835, filed on Nov. 7, 2016.

(60) Provisional application No. 62/415,952, filed on Nov. 1, 2016, provisional application No. 62/279,126, filed on Jan. 15, 2016.

(51) Int. Cl.
*C12Q 1/6869* (2018.01)
*C12Q 1/6874* (2018.01)

(52) U.S. Cl.
CPC ......... *C12Q 1/6874* (2013.01); *C12Q 1/6869* (2013.01)

(58) Field of Classification Search
None
See application file for complete search history.

(56) References Cited

U.S. PATENT DOCUMENTS

| 2011/0033854 A1 | 2/2011 | Drmanac et al. |
| 2012/0178634 A1 | 7/2012 | Sakai |
| 2015/0126379 A1 | 5/2015 | Liang et al. |

FOREIGN PATENT DOCUMENTS

| CN | 101932729 A | 12/2010 |
| EP | 3564395 A1 | 11/2019 |
| JP | 2013520202 A | 6/2013 |
| WO | 2009061840 A1 | 5/2009 |
| WO | 2009076238 A2 | 6/2009 |
| WO | 2009099602 A1 | 8/2009 |
| WO | 2011002029 A1 | 1/2011 |
| WO | 2011106314 A2 | 9/2011 |
| WO | 2012024658 A2 | 2/2012 |
| WO | 2017123316 A1 | 7/2017 |

OTHER PUBLICATIONS

Burden (Random Primers issue Jan. 12 25 pages) (Year: 2012).*
Broude et al (PNAS 91:3072-6). (Year: 1994).*
2006 Qiagen DNAeasy® Blood & Tissue kit Handbook (Year: 2006).*
Blaud-Rotureau et al, 2002, "A Comparative Analysis of FISH, RT-PCR, PCR, and Immunohistochemistry for the Diagnosis of Mantle Cell Lymphomas", Modern Pathology, 15(5): 517-525.
Burden, David W., Ph.D., 2012, "Guide to the Disruption of Biological Samples", Random Primers, Jan. 2012, 12:1-25.
Bzhalava et al, 2014, "Deep sequencing extends the diversity of human papillomaviruses in human skin", Scientific Reports, 4(24):5807.
Casbon et al, 2011, "A method for counting PCR template molecules with application to next-generation sequencing", Nucleic Acids Research, 39(12):e81.
Cottrell et al, 2014, "Validation of a Next-Generation Sequencing Assay for Clinical Molecular Oncology", The Journal of Molecular Diagnostics, 16(1):89-105.
International Search Report and Written Opinion dated Apr. 20, 2017 in corresponding PCT/US2016/060861 filed Nov. 7, 2016 (33334 WO), pp. 1-18.
International Search Report and Written Opinion dated Jan. 23, 2017 in connection with PCT/US2016/060835 filed Nov. 7, 2016, 13 pages.
Kim et al, 2013, "A Microfluidic DNA Library Preparation Platform for Next-Generation Sequencing", PLOS One, 8(7):e68988.
Mansour et al., 2014, "A novel xylene-free deparaffinization method for the extraction of proteins from human derived formalin-fixed paraffin embedded (FFPE) archival tissue blocks", MethodsX, 1:90-95.
Mattsson et al., 2007, "Detection of Genetic Alterations by ImmunoFISH Analysis of Whole Cells Extracted from Routine Biopsy Material", Journal of Molecular Diagnostics, 9(4): 479-489, vol. 9, No. 4.
Pareek et al, 2011, "Sequencing technologies and genome sequencing", Journal of Applied Genetics, 52(4):413-435.
Thaitrong et al, 2012, "Quality control of next-generation sequencing library through an integrative digital microfluidic platform", Electrophoresis, 2012, 33:3506-3513.
Yang, et al., "An efficiency analysis of high-order combinations of gene-gene interactions using multifactor-dimensionality reduction," BMC Genomics (2015) 16:489; DOI 10.1186/s12864-015-1717-8.
Alito, "A comprehensive assessment of somatic mutation detection in cancer using whole-genome sequencing," Nature Communications, published Dec. 9, 2015; DOI: 10.1038/ncomms10001.
Peng, "Reducing amplification artifacts in high multiplex amplicon sequencing by using molecular barcodes," BMC Genomics (2015) 16:589; DOI 10.1186/s12864-015-1806-8.
Wei Li et al., Molecular Diagnostic, pp. 102-103, China Medical Science and Technology Press, Sep. 30, 2015 (including a machine translation).

* cited by examiner

*Primary Examiner* — Christopher M Gross
(74) *Attorney, Agent, or Firm* — Charney IP Law LLC; Thomas M. Finetti

(57) ABSTRACT

In one aspect of the present disclosure is a targeted sequencing workflow where an input sample comprising a sufficient quantity of genomic material is provided such minimal or no amplification cycles are utilized prior to sequencing.

19 Claims, 12 Drawing Sheets

DEEP SEQUENCING PROFILING OF TUMORS

CROSS REFERENCE TO RELATED APPLICATIONS

This application is a continuation of International Patent Application No. PCT/US2016/060835 filed Nov. 7, 2016, which claims priority to and the benefit of U.S. Provisional Patent Application No. 62/415,952, filed Nov. 1, 2016 and the benefit of the filing date of U.S. Provisional Patent Application No. 62/279,126, filed Jan. 15, 2016, the disclosures of which are hereby incorporated by reference herein in their entireties.

FIELD OF THE SUBJECT DISCLOSURE

The present disclosure provides a targeted representational sequencing workflow.

BACKGROUND

Current diagnostic oncology utilizes information taken from a fraction of a tumor and is predicated on the assumption that tumors are composed of cells that are uniform in their composition. Rather than being uniform in composition, many tumors are heterogeneous. Indeed, it has been reported that some solid tumors, rather than being homogeneous, are composed of multiple genetically distinct, spatially segregated populations of cancer cells. See Gerlinger et al., NEJM (2012) 366:883-92; and Yachida et al. Nature (2010) 467(7319):1114-1117. Conventional histological methodologies address this heterogeneity with the selection of multiple biopsy samples for analysis, e.g., based on morphology and other characteristics. For example, biopsy samples are taken from multiple regions of the tumor, wherein each sample taken comprises about 0.1 cubic centimeter of tissue. These methods survey more of the tumor tissue and different spatial areas of the tumor; however, the vast majority of the tumor assayed using such methods remains un-sampled. Similarly, conventional methods sample only a small portion of the lymph nodes from cancer patients and do not sample the vast majority of the tissue. The small size of these samples can also be limiting on the further diagnostic steps that are utilized, such as sequencing.

Solid tumors contain hundreds to thousands of mutant alleles that are spatially segregated throughout the three-dimensional tumor mass. Traditional methods for sequence capture utilize extremely small amounts of input DNA (about 5 to about 200 nanograms) isolated from formalin fixed, paraffin embedded tissue sections (e.g. from biopsy specimens), such as depicted in FIG. 2. Typical sequence capture methods have evolved to fit the input DNA requirements in today's clinical pathology labs. Due to the small amounts of input DNA, and loss of DNA at several steps in the sequence capture workflow, the DNA fragments must be amplified or too little will remain at the end of the capture workflow for sequencing to be performed. This amplification generally is performed twice, a first time prior to the specific probe capture, and a second time following the specific probe capture of the selected targets (see FIGS. 1 and 2). While this amplification is useful for increasing the absolute mass of the DNA available for subsequent protocol steps, it does not increase the amount of information present. Rather, and without wishing to be bound by any particular theory, when a population of different DNA fragments is amplified in the same reaction (i.e. multiplex PCR), the process of amplification can alter the information that was contained within the original sample. For example, if two different DNA fragments, A and B, are initially present in a sample at one copy each (a 1:1 numerical ratio), PCR may result in an amplified sample that contains 1,000 copies of DNA fragment A and 2,000 copies of DNA fragment B (a 1:2 numerical ratio). It is believed that the risk of introducing bias to the original information is increased when smaller numbers of individual molecules are used as input into the amplification process and when the amount of amplification is increased (i.e. a greater number of PCR cycles are applied).

BRIEF SUMMARY OF THE DISCLOSURE

In one aspect of the present disclosure is a targeted sequencing workflow where an input sample comprising a sufficient quantity of genomic material is provided such that minimal or no amplification processes are required prior to sequencing. In some embodiments, the input sample is derived from an intact tumor or from lymph nodes. In some embodiments, the input sample is obtained through homogenization of an intact tumor sample (whole or partial) and/or one or more lymph nodes obtained from a patient or mammalian subject, as discussed further herein. In some embodiments, the input sample is derived from a sufficient quantity of blood, including whole blood or any fraction thereof. In some embodiments, the input sample is derived from cancerous tissue. In some embodiments, the input sample is derived from pre-cancerous tissue.

In some embodiments, the targeted sequencing workflow comprises one or more amplification steps (e.g. a pre-capture amplification step, an amplification step post-capture) prior to sequencing, where each amplification step prior to sequencing comprises from 0 to 3 amplification cycles, and wherein an aggregate of amplification cycles prior to sequencing does not exceed 4. In other embodiments, the targeted sequencing workflow comprises one or more amplification steps (e.g. a pre-capture amplification step, an amplification step post-capture) prior to sequencing, where each amplification step prior to sequencing comprises from 0 to 2 amplification cycles, and wherein an aggregate of amplification cycles prior to sequencing does not exceed 3. In yet other embodiments, the targeted sequencing workflow comprises one amplification step prior to sequencing (e.g. either a pre-capture amplification step or an amplification step post-capture), where the single amplification step prior to sequencing comprises from 0 to 3 amplification cycles. In further embodiments, the targeted sequencing workflow comprises one amplification step prior to sequencing, where the single amplification step prior to sequencing comprises from 1 to 3 cycles. In yet further embodiments, the targeted sequencing workflow comprises one amplification step prior to sequencing, where the single amplification step prior to sequencing comprises 1 cycle. In even further embodiments, the targeted sequencing workflow comprises one amplification step prior to sequencing, where the single amplification step prior to sequencing comprises 2 cycles. In some embodiments, either or both of the pre-capture amplification step or the amplification step post-capture but prior to sequencing utilizes LM-PCR.

In some embodiments, the input sample comprises a representative sampling of cells derived from a tumor sample, lymph node sample, blood sample, or any combination thereof. In some embodiments, the input sample comprises a representative sample of cells derived from a tumor sample, lymph node sample, blood sample, or any combination thereof from a patient or mammalian subject diagnosed with cancer. In some embodiments, the input sample comprises a representative sample of cells derived from a tumor sample, lymph node sample, blood sample, or any combination thereof from a patient or mammalian subject suspected of having cancer. In some embodiments, the input sample comprises a representative sample of cells derived from a tumor sample, lymph node sample, blood sample, or any combination thereof from a patient or mammalian subject at risk of developing cancer. In some embodiments, the input sample comprises a representative sample of cells within a tumor sample, lymph node sample, blood sample, or any combination thereof from a patient or mammalian subject where a relapse or recurrence of cancer is known or suspected.

In some embodiments, the input sample comprises a heterogeneous population of cells from derived from a tumor sample, lymph node sample, or blood sample. In some embodiments, the input sample comprises subclones (i.e. different tumor cell populations that arise as a result of tumor instability) representing a minority of certain tumor cell populations from within the tumor sample, lymph node sample, or blood sample. In some embodiments, the method allows for the detection and/or sequencing of rare genomic variants, such as those having less than 2% allele frequency in the input sample. In some embodiments, the method allows for the detection and/or sequencing of rare genomic variants, such as those having less than 1% allele frequency in the input sample.

In some embodiments, the input sample is derived from a sufficient quantity of histological sections and/or biopsy samples, e.g. obtained from multiple histological sections and/or multiple biopsy samples. In some embodiments, the input sample derived from histological sections and/or biopsy samples comprise at least 0.5 micrograms of genomic material. In other embodiments, the input sample derived from histological sections and/or biopsy samples comprise at least 1 microgram of genomic material. In other embodiments, the input sample derived from histological sections and/or biopsy samples comprise at least 5 micrograms of genomic material. In other embodiments, the input sample derived from histological sections and/or biopsy samples comprise at least 10 micrograms of genomic material.

In some embodiments, the quantity of genomic material within the input sample for use with the disclosed methods is at least 10 times greater than a quantity of material within an input sample for use with traditional sequence capture methods. In some embodiments, the quantity of genomic material within the input sample for use with the disclosed methods is at least 100 times greater than a quantity of material within an input sample for use with traditional sequence capture methods. In some embodiments, the quantity of genomic material within the input sample for use with the disclosed methods is at least 250 times greater than a quantity of material within an input sample for use with traditional sequence capture methods. In some embodiments, the quantity of genomic material within the input sample for use with the disclosed methods is at least 500 times greater than a quantity of material within an input sample for use with traditional sequence capture methods. In some embodiments, the quantity of genomic material within the input sample for use with the disclosed methods is at least 1000 times greater than a quantity of material within an input sample for use with traditional sequence capture methods. In some embodiments, the quantity of genomic material within the input sample for use with the disclosed methods is about 1000 times greater than a quantity of material within an input sample for use with traditional sequence capture methods.

In another aspect of the present disclosure is a method of sequencing genomic material within a sample comprising: homogenizing a tumor sample and/or lymph node sample to provide a homogenized sample; isolating at least 0.5 micrograms of genomic material from the homogenized sample; preparing the at least 0.5 micrograms of isolated genomic material for sequencing; and sequencing the prepared genomic material. In some embodiments, the method does not comprise any amplification steps prior to sequencing. In some embodiments, the method comprises at least one pre-capture or post-capture amplification step, wherein an aggregate number of amplification cycles conducted during the at least one pre-capture or post-capture amplification step is at most 4 cycles. In some embodiments, the aggregate number of amplification cycles is 3. In some embodiments, the aggregate number of amplification cycles is 2. In some embodiments, the preparing of the at least 0.5 micrograms of isolated genomic material for sequencing comprises hybridizing the at least 0.5 micrograms of isolated genomic to capture probes and capturing the hybridized genomic material. In some embodiments, an amount of captured genomic material ranges from about 90 ng to about 900 ng. In some embodiments, 1 or 2 amplification cycles are performed on the captured genomic material. In some embodiments, the homogenized sample comprises a representative sampling of cells. In some embodiments, at least 1 microgram of genomic material is isolated from the homogenized samples. In some embodiments, at least 5 micrograms of genomic material is isolated from the homogenized samples. In some embodiments, at least 10 micrograms of genomic material is isolated from the homogenized samples.

In another aspect of the present disclosure is a method of sequencing DNA within a sample comprising isolating at least 0.5 micrograms of DNA from a blood sample; preparing the at least 0.5 micrograms of isolated DNA for sequencing, and sequencing the prepared DNA. In some embodiments, the method comprises 0 amplification steps prior to sequencing. In some embodiments, the preparing of the at least 0.5 micrograms of isolated DNA for sequencing comprises hybridizing the at least 0.5 micrograms of isolated genomic to capture probes and capturing the hybridized genomic material. In some embodiments, an amount of captured genomic material ranges from about 90 ng to about 900 ng. In some embodiments, 1 or 2 amplification cycles are performed on the captured genomic material. In some embodiments, at least 1 microgram of DNA is isolated from the blood sample.

In another aspect of the present disclosure is a method of targeted representational sequencing comprising: (i) homogenizing at least a portion of a tumor, one or more whole or partial lymph nodes, or any combination thereof to provide a homogenized sample; (ii) extracting genomic material from the homogenized sample; (iii) capturing the extracted genomic material onto beads; and (iv) sequencing the captured genomic material; wherein the targeted representational sequencing comprises performing at most 4 amplification cycles prior to sequencing of the captured genomic material. In some embodiments, the at most 3 amplification cycles may be conducted prior to capture of the extracted genomic material or after capture of the extracted genomic material, or any combination thereof. In some embodiments, no pre-capture amplification cycles are conducted. In some embodiments, an amount of captured genomic material ranges from about 90 ng to about 900 ng. In some embodiments, from 1 to 3 amplification cycles are performed following capture of the extracted genomic material, but prior to sequencing. In some embodiments, at least 0.5 micrograms of genomic material is extracted from the homogenized sample. In some embodiments, at least 100 times more genomic material is derived from the homogenized sample as compared with an amount of input material used in a sequencing method requiring more than 4 amplification cycles.

In another aspect of the present disclosure is a method of sequencing DNA within a sample comprising: providing at least 0.5 micrograms of input genomic material, the at least 0.5 micrograms of genomic material derived from a tumor sample, a lymph node sample, or a blood sample, isolating DNA from the input genomic sample, preparing the isolated DNA for sequencing, and sequencing the prepared DNA, wherein the method does not comprise any amplification steps. In some embodiments, the at least 0.5 micrograms of input genomic material is derived from multiple histological and/or biopsy specimens. In some embodiments, the at least 0.5 micrograms of input genomic material is derived from a homogenized tumor sample. In some embodiments, the at least 0.5 micrograms of input genomic material is derived from a homogenized lymph node sample. In some embodiments, the at least 0.5 micrograms of input genomic material is a representative sampling of the tumor sample, lymph node sample, or blood sample from which it is derived. In some embodiments, the sequencing is performed using a next-generation sequencing method. In some embodiments, sequencing is performed using a synthesis sequencing methodology.

In another aspect of the present disclosure is a method of reducing PCR-introduced mutations during sequencing comprising isolating DNA from a sample comprising a sufficient amount of genomic material; preparing the isolated DNA for sequencing; and sequencing the prepared DNA, wherein the method comprises at most 3 amplification cycles prior to sequencing. In some embodiments, the method comprises 1 or 2 amplification cycles prior to sequencing. In some embodiments, sufficient amount of input genomic material is an amount such that no pre-capture amplification cycles are utilized. In some embodiments, the sample is derived from a patient suspected of having cancer. In some embodiments, the sample is derived from a patient diagnosed with cancer. In some embodiments, the sample is derived from a patient at risk of developing cancer. In some embodiments, the sample is derived from healthy tissue samples. In some embodiments, 0.5 micrograms of DNA is isolated from the sample. In some embodiments, at least 1 microgram of genomic material is isolated from the sample. In some embodiments, at least 5 micrograms of genomic material is isolated from the sample. In some embodiments, at least 10 micrograms of genomic material is isolated from the sample.

In another aspect of the present disclosure is a sequencing method where PCR-introduced mutations are reduced, the sequencing method comprising capturing at least 0.05 micrograms of genomic material, and performing between 0 and 2 amplification cycles prior to sequencing. In some embodiments, 0 amplification cycles are conducted. In other embodiments, 1 amplification cycle is conducted. In yet other embodiments, 2 amplification cycles are conducted.

In another aspect of the present disclosure is a sequence capture method where PCR-introduced biases in the proportional representation of genome content are reduced, the sequencing method comprising providing an input sample comprising at least 0.5 micrograms of genomic material, and where the sequence capture method comprises performing between 0 and 2 amplification cycles prior to sequencing. In some embodiments, 0 amplification cycles are conducted. In other embodiments, 1 amplification cycle is conducted. In yet other embodiments, 2 amplification cycles are conducted. In some embodiments, the input sample comprises at least 1 microgram of genomic material. In some embodiments, the input sample comprises at least 5 micrograms of genomic material. In some embodiments, the input sample comprises at least 10 micrograms of genomic material.

In another aspect of the present disclosure is a sequence capture method where PCR-introduced mutations are eliminated, the sequence capture method comprising preparing an input sample comprising at least 0.5 micrograms of genomic material. In some embodiments, the input sample comprises at least 1 microgram of genomic material. In some embodiments, the input sample comprises at least 5 micrograms of genomic material. In some embodiments, the input sample comprises at least 10 micrograms of genomic material.

In another aspect of the present disclosure is a sequence capture method where a step of removing PCR-duplicate reads prior to sequencing is eliminated, the sequence capture method comprising providing an input sample comprising at least 0.5 micrograms of genomic material. In some embodiments, the input sample comprises at least 1 microgram of genomic material. In some embodiments, the input sample comprises at least 5 micrograms of genomic material. In some embodiments, the input sample comprises at least 10 micrograms of genomic material.

In another aspect of the present disclosure is a sequencing method where PCR-introduced mutations are virtually eliminated, the sequencing method comprising capturing at least 0.05 micrograms of genomic material. In some embodiments, about 0.05 micrograms of genomic material are provided after capture of the genomic material. In some embodiments, 1 or 2 post-capture amplification cycles are performed prior to sequencing.

In another aspect of the present disclosure is a method of treating cancer by identifying cancer subtypes responsive to a particular treatment or active pharmaceutical ingredient, wherein the cancer subtype is identified by sequencing an input sample comprising a representative sampling of a tumor, lymph node, or blood; the input sample comprising a sufficient quantity of genomic material, and wherein the step of sequencing requires at most 3 amplification cycles.

As noted herein, traditional sequencing workflows may introduce certain biases. In some instances, a PCR-induced bias in the information content of an amplified DNA sample may be maintained when the sample is sequenced using next-generation sequencing (NGS) methods. The application of NGS to a population of amplified DNA fragments thus results in two drawbacks, namely (1) a large number of sequencing reads are expended in the redundant sequencing of copies of the same original fragment, which is not cost effective, and (2) the numerical biases introduced by the amplification process can lead to misrepresentation of the information present in the original unamplified sample, and this is especially important when the primary purpose of the targeted sequencing assay is to accurately determine the presence and relative frequency of different DNA sequences in a sample. An additional drawback with PCR amplification of DNA fragments prior to NGS is that the PCR process can generate sequence errors while copying the original fragments, and these may then be interpreted as having been present in the original sample.

Applicants have developed a sequence capture workflow which improves or mitigates upon the aforementioned drawbacks by (i) minimizing the number of amplification cycles utilizes prior to sequencing, or (ii) avoiding amplification steps altogether prior to sequencing. The method for targeted representational sequencing of tumors presented herein utilizes sufficient amounts of input genomic DNA, and/or efficient enzymatic fragmentation-based library preparation, to remove or greatly reduce the need to amplify that DNA during the workflow (see FIGS. 3A, 3B, and 4). This in turn is believed to facilitate cost-effective characterization of the sample (as sequencing reads are not wasted on sequencing of duplicated DNA fragments), reduce the opportunity for amplification induced bias in the output sequence data, and/or reduce the opportunity for PCR induced errors to lead to false-positives in the sequencing data. Indeed, Applicants have unexpectedly discovered that a reduction or elimination of pre-capture and post-capture PCR from the workflow reduces (i) the cost of targeted sequencing (removing the cost of PCR primers, PCR reaction buffers, and PCR enzymes); (ii) reduces the assay time; (iii) reduces the risk of sample-to-sample contamination (a well-known risk of the PCR process); (iv) removes or mitigates the risk of representational bias in the sequence data due to differential amplification of targeted fragments; (v) removes or mitigates the risk of false-positive sequence variants caused by polymerase errors during PCR amplification; and/or (vi) facilitates a simpler, faster, and/or less error prone data analysis and interpretation.

Applicants further submit that the methods disclosed herein unexpectedly reduce or prevent allelic and locus bias in sequence coverage as would otherwise be introduced through amplification, such as may be introduced via the process illustrated in FIG. 1. Thus, Applicants believe the presently disclosed method provides for a superior method (i.e. one that is more accurate) of measuring allele frequencies and copy number variations in cancer genomics. Applicants also submit that the methods disclosed herein allow sequencing with a reduced need of identifying and removing redundant sequence reads in analysis of the sequence data. These factors are especially important for the accurate measurement of somatic allele frequencies and copy number variation present in the genomic DNA of cancer patients.

BRIEF DESCRIPTION OF THE DRAWINGS

Non-limiting and non-exhaustive embodiments are described with reference to the following drawings.

DETAILED DESCRIPTION

Figure 1:
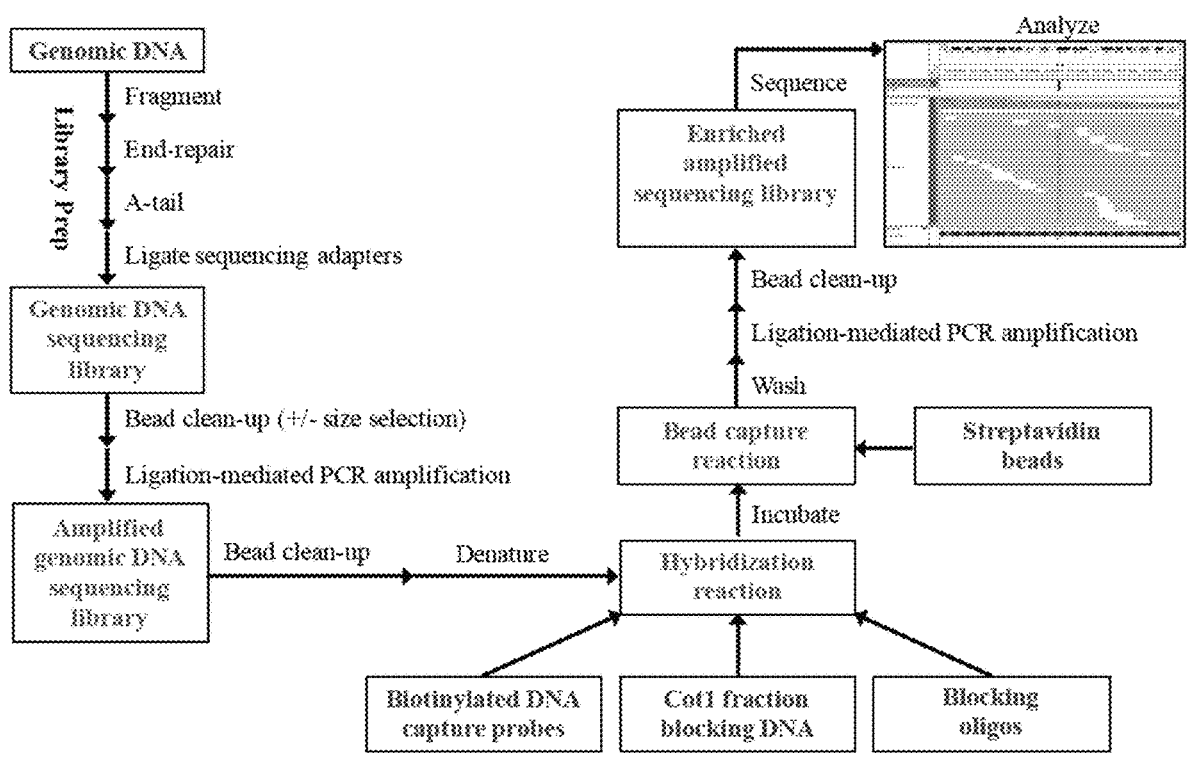
FIG. 1 sets forth a sequence capture workflow incorporating two amplification steps.

In general, the present disclose provides a targeted representational sequencing workflow where the number of amplification cycles are at least minimized as compared with traditional sequencing methods. Without wishing to be bound by any particular theory, it is believed that one way to reduce the number of pre-capture and/or post-capture PCR amplification cycles prior to sequencing is to increase the quantity of input DNA provided into the system, as disclosed further herein. Applicants submit that the present sequencing workflow reduces the risk of (i) of the introduction of mutations due to the intrinsic low rate of misincorporation of nucleotides, and (ii) an altered representation of target sequences due to PCR amplification bias.

As used herein, the singular terms "a," "an," and "the" include plural referents unless the context clearly indicates otherwise. Similarly, the word "or" is intended to include "and" unless the context clearly indicates otherwise.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

The term "amplification," as used herein, refers to a process of multiplying an original quantity of a nucleic acid template in order to obtain greater quantities of the original nucleic acid.

Likewise, the term "amplifying" refers to a process whereby a portion of a nucleic acid is replicated using, for example, any of a broad range of primer extension reactions. Exemplary primer extension reactions include, but are not limited to, polymerase chain reaction (PCR). Unless specifically stated, "amplifying" refers to a single replication or to an arithmetic, logarithmic, or exponential amplification. In general, PCR is a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers are then annealed to their complementary sequences within the target molecule. Following annealing, the primers are extended with a polymerase (e.g. DNA polymerase) so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment (the amplicon) of the desired target sequence. The length of the amplified segment of the desired target sequence is determined by the relative positions of the primers with respect to each other, and therefore, this length is a controllable parameter. Polymerase chain reaction ("PCR") is described, for example, in U.S. Pat. No. 4,683,202; U.S. Pat. No. 4,683,195; U.S. Pat. No. 4,000,159; U.S. Pat. No. 4,965,188; U.S. Pat. No. 5,176,995), the disclosures of each are hereby incorporated by reference herein in their entirety.

The phrase "biases in the proportional representation of genome content" refers to a tendency for parts of a genome to become underrepresented after amplification, such as those parts that are more difficult for polymerase to copy.

The term "hybridization," as used herein refers to the process of joining two complementary strands of DNA or one each of DNA and RNA to form a double-stranded molecule through Watson and Crick base-pairing or pairing of a universal nucleobase with one of the four natural nucleobases of DNA (adenine, guanine, thymine and cytosine).

The term "next generation sequencing (NGS)" refers to sequencing technologies having high-throughput sequencing as compared to traditional Sanger- and capillary electrophoresis-based approaches, wherein the sequencing process is performed in parallel, for example producing thousands or millions of relatively small sequence reads at a time. Some examples of next generation sequencing techniques include, but are not limited to, sequencing by synthesis, sequencing by ligation, and sequencing by hybridization. These technologies produce shorter reads (anywhere from 25-500 bp) but many hundreds of thousands or millions of reads in a relatively short time. The term "next-generation sequencing" refers to the so-called parallelized sequencing-by-synthesis or sequencing-by-ligation platforms currently employed by Illumina, Life Technologies, and Roche etc. Next-generation sequencing methods may also include nanopore sequencing methods or electronic-detection based methods such as Ion Torrent technology commercialized by Life Technologies.

The term "nucleic acid" as used herein, refers to a high-molecular-weight biochemical macromolecule composed of nucleotide chains that convey genetic information. The most common nucleic acids are deoxyribonucleic acid (DNA) and ribonucleic acid (RNA). The monomers from which nucleic acids are constructed are called nucleotides. Each nucleotide consists of three components: a nitrogenous heterocyclic base, either a purine or a pyrimidine (also known as a nucleobase); and a pentose sugar. Different nucleic acid types differ in the structure of the sugar in their nucleotides; DNA contains 2-deoxyribose while RNA contains ribose.

The term "polymerase" as used herein, refers to an enzyme that catalyzes the process of replication of nucleic acids. More specifically, DNA polymerase catalyzes the polymerization of deoxyribonucleotides alongside a DNA strand, which the DNA polymerase "reads" and uses as a template. The newly-polymerized molecule is complementary to the template strand and identical to the template's partner strand.

As used herein, "sequencing" or "DNA sequencing" refers to biochemical methods for determining the order of the nucleotide bases, adenine, guanine, cytosine, and thymine, in a DNA oligonucleotide. Sequencing, as the term is used herein, can include without limitation parallel sequencing or any other sequencing method known of those skilled in the art, for example, chain-termination methods, rapid DNA sequencing methods, wandering-spot analysis, Maxam-Gilbert sequencing, dye-terminator sequencing, or using any other modern automated DNA sequencing instruments.

The term "sequencing library" refers to a collection of nucleic acid fragments from a genome, sheared to even length and added adaptor and index sequence on both ends for NGS.

As used herein, the phrase "target sequence" refers to a region of a nucleic acid which is to be amplified, detected, or otherwise analyzed.

Input Sample

In general, the input sample utilized as part of the sequencing workflow disclosed herein is derived from or prepared from a tumor sample, e.g. an intact tumor, and/or from lymph nodes. The term "tumor sample" encompasses samples prepared from a tumor or from a sample potentially comprising or suspected of comprising cancer cells, or to be tested for the potential presence of cancer cells, such as a lymph node. In some embodiments, the input sample is derived by homogenizing (as described herein) a tumor sample (whole or partial) and/or one or more lymph notes obtained from a patient or mammalian subject, as discussed further herein. In other embodiments, the input sample is derived from blood, e.g. whole blood or a constituent part of whole blood. In some embodiments, the input sample is derived from histological sections or biopsy samples, e.g. from multiple histological sections or multiple biopsy samples.

In some embodiments, the input sample is a representative sampling of cells within a tumor (e.g. a tumor sample), lymph nodes, or blood. The terms "representative sample" and "representative sampling" as used herein refer to a sample (or a subset of a sample) that accurately reflects the components of the entirety and, thus, the sample is an unbiased indication of the entire population. In general, this means that the different types of cells and their relative proportion or percentages within the representative sample or a portion thereof essentially accurately reflects or mimics the relative proportion or percentages of these cell types within the entire tissue specimen, generally a solid tumor or portion thereof. Sampling is the operation of securing portions of an object for subsequent analysis. Representative samples are generated in a way that a reasonably close knowledge of the object being studied can be obtained. By contrast, conventional random sampling methods, generally does not give rise to a "representative sample." While the selection of smaller individual sub-samples from a larger sample can be biased based on the regions selected, homogenizing a large sample, e.g., an entire tumor or lymph node, results in spatially segregated elements being homogenously dispersed throughout the sample.

In some embodiments, the input sample comprises a representative sample of cells derived from a tumor sample, lymph node sample, blood sample, or any combination thereof from a patient or mammalian subject diagnosed with cancer. In some embodiments, the input sample comprises a representative sample of cells derived from a tumor sample, lymph node sample, blood sample, or any combination thereof from a patient or mammalian subject suspected of having cancer. In some embodiments, the input sample comprises a representative sample of cells derived from a tumor sample, lymph node sample, blood sample, or any combination thereof from a patient or mammalian subject at risk of developing cancer. In some embodiments, the input sample comprises a representative sample of cells within a tumor sample, lymph node sample, blood sample, or any combination thereof from a patient or mammalian subject where a relapse or recurrence of cancer is known or suspected. In some embodiments, the input sample comprises a representative sampling of cells within a tumor sample, lymph node sample, or blood sample from a patient at risk of developing cancer. In some embodiments, the input sample comprises a representative sampling of cells within a tissue sample or a blood sample from a healthy patient. In some embodiments the input sample comprises a number of histological sections sufficient to purify the required amount of DNA.

In one embodiment, the representative examples disclosed herein are obtained by homogenization of large volumes or quantities of a tumor sample (such as a clinical tumor sample) or lymph node obtained from a subject. For example, the whole tumor or a substantial portion thereof may be used as the input material from which the representative sample is generated. In some embodiments, at least 40% of a tumor or lymph node (or the portion thereof that remains after removal of portions for the conduct of other diagnostic tests, such as removal of a portion usable for preparation of conventional FFPE samples) is utilized for homogenization. In other embodiments, at least 50% of a tumor or lymph node is utilized for homogenization. In other embodiments, at least 60% of a tumor or lymph is utilized for homogenization. In other embodiments, at least 70% of a tumor or lymph node is utilized for homogenization. In other embodiments, at least 80% of a tumor or lymph is utilized for homogenization. In other embodiments, at least 90% of a tumor or lymph node is utilized for homogenization. In other embodiments, at least 95% of a tumor or lymph node is utilized for homogenization. In yet other embodiments, the entire tumor, an entire lymph node, or an entire population of lymph nodes (or the portion thereof that remains after removal of portions for the conduct of other diagnostic tests, such as removal of a portion usable for preparation of conventional FFPE samples), is used for homogenization.

The representative sample may be generated from an intact tumor biopsy sample from a solid tumor. In some embodiments, the biopsy sample comprises at least about 100-200 cells. In other embodiments, the biopsy sample comprises at least about 200-1,000 cells. In yet other embodiments, the biopsy sample comprises at least about 1,000-5,000 cells. In further embodiments, the biopsy sample comprises at least about 10,000-100,000 cells. In even further embodiments, the biopsy sample comprises at least about 100,000-1,000,000 or more cells. In some embodiments, the cells are obtained from spatially distinct regions of the tumor. In another embodiment, the representative examples disclosed herein are obtained by homogenization of one or more putative normal tissue specimens, e.g., derived from a patient or mammalian subject at risk of developing cancer, including those at risk of developing cancer because of a genetic mutation or prior cancer. As used herein, the term "spatially distinct" refers to elements that are distributed in different regions of a space. In one embodiment, the tumor biopsy samples used to generate the representative sample are taken from different regions of the tumor sample. For example, proximal versus distal regions of the tumor, different faces of the tumor, different layers of the tumor, etc. in an effort to capture the diversity within the whole tumor.

The terms "homogenizing" or "homogenization" refer to a process (such as a mechanical process and/or a biochemical process) whereby a biological sample is brought to a state such that all fractions of the sample are equal in composition. Representative samples (as defined above) may be prepared by removal of a portion of a sample that has been homogenized. A homogenized sample (a "homogenate") is mixed well such that removing a portion of the sample (an aliquot) does not substantially alter the overall make-up of the sample remaining and the components of the aliquot removed is substantially identical to the components of the sample remaining. In the present disclosure the "homogenization" will in general preserve the integrity of the majority of the cells within the sample, e.g., at least 50% of the cells in the sample will not be ruptured or lysed as a result of the homogenization process. In other embodiments, homogenization will preserve the integrity of at least 80% of the cells in the sample. In other embodiments, homogenization will preserve the integrity of at least 85% of the cells in the sample. In other embodiments, homogenization will preserve the integrity of at least 90% of the cells in the sample. In other embodiments, homogenization will preserve the integrity of at least 95% of the cells in the sample. In other embodiments, homogenization will preserve the integrity of at least 96 of the cells in the sample. In other embodiments, homogenization will preserve the integrity of at least 97% of the cells in the sample. In other embodiments, homogenization will preserve the integrity of at least 98% of the cells in the sample. In other embodiments, homogenization will preserve the integrity of at least 99% of the cells in the sample. In other embodiments, homogenization will preserve the integrity of at least 99.9% of cells in the same. The homogenates may be substantially dissociated into individual cells (or clusters of cells) and the resultant homogenate or homogenates are substantially homogeneous (consisting of or composed of similar elements or uniform throughout).

In some embodiments, a tumor sample, lymph node sample, or other tissue sample is homogenized by placing the sample into a mechanical shearing apparatus, e.g. a blender or an ultra sonicator. The homogenization produces a range of tissue fragments from thousands to hundreds of cells each, likely fitting to a normal distribution. The median of the tissue fragment size is inversely correlated to the energy of the blender (or other suitable device); such that at high energy the tissue fragments are very small. The component of the tissue that is most relevant to blender energy is collagen content, as the dermis requires significant energy for complete disassociation. The time of blending is also important; however, the most effective clinical application requires that the whole tumor be disassociated in a matter of minutes. Once the time of blending is fixed, the energy required to reach tumor disassociation under the desired time limit can readily be determined. Other methods of preparing tumor samples or lymph node samples are disclosed in co-pending United States provisional patent applications, namely Application Nos. 62/252,153 (filed Nov. 6, 2015), 62/279,405 (filed Jan. 15, 2016) and 62/354,622 (filed Jun. 24, 2016) (each assigned to Ventana Medical Systems, Inc. (Tucson, Ariz.), the disclosures of which are incorporated herein by reference, each in their entirety. Test samples can be taken from the homogenized sample for use in the sequencing workflow described herein, namely as the input sample comprising genomic material.

Following sufficient mechanical shearing to disassociate the tumor, lymph node, or other tissue sample, all of the subpopulations of tumor cells that were originally spatially segregated are distributed throughout the newly homogenized sample. That is, as a result of homogenizing a tumor sample (or homogenization of a lymph node), any heterogeneity of cells within the tumor is substantially homogeneously (uniformly) distributed within the resultant homogenate or a portion or fraction thereof, such that the homogenate (or any fraction thereof) substantially homogeneously expresses the heterogeneity of the tumor biopsy sample which was the input. By homogenizing tumors or lymph nodes to generate a sample (or homogenate) that is representative of the tumor in its entirety, it is possible to characterize the landscape (such as the heterogeneity) of the tumor and/or to sequence each of the different genomic subpopulations contained throughout.

In some embodiments, the input sample comprises a heterogeneous population of cells from derived from a tumor sample, lymph node sample, or blood sample. In some embodiments, the input sample comprises subclones (i.e. different tumor cell populations that arise as a result of tumor instability) representing a minority of certain tumor cell populations from within the tumor sample, lymph node sample, or blood sample. In some embodiments, the method allows for the detection and/or sequencing of rare genomic variants, such as those having less than 2% allele frequency in the input sample. In some embodiments, the method allows for the detection and/or sequencing of rare genomic variants, such as those having less than 1% allele frequency in the input sample.

In some embodiments, the homogenized sample is further processed prior to use in the sequencing workflow, such as by separating cells or genomic material. In some embodiments, the homogenized sample is first filtered.

In some embodiments, cells within the homogenized sample, or filtered homogenized sample, are lysed to release cellular components. For example, cells may be lysed using a French press or similar type of lysis apparatus, microfluidizers, grinding, milling, chemical or enzymatic lysis, and/or using other techniques known in the art. In some embodiments, membrane lipids and proteins (include histones) are removed from the sample containing the cellular components (e.g. by adding surfactants or enzymes (proteases)). In addition, RNA may be removed from the sample containing the cellular components (e.g. with an enzyme such as an RNase).

In some embodiments, DNA may be isolated, extracted, or purified by means known to those of ordinary skill in the art. For example, DNA may be extracted via ethanol precipitation or phenol-chloroform extraction followed by centrifugation to form a pellet. In some embodiments, the DNA may be isolated or extracted on a solid phase column. In some embodiments, the DNA may be isolated or extracted using nucleic acid-binding beads. In some embodiments, the DNA may be isolated or extracted by selective passage through a porous matrix based on physical, chemical, or electrical properties.

The extracted DNA (genomic material) may be dissolved in a buffer, e.g. an alkaline buffer, and introduced as the input sample for sequencing, as explain further herein.

Sequencing Workflow

Figure 3A:
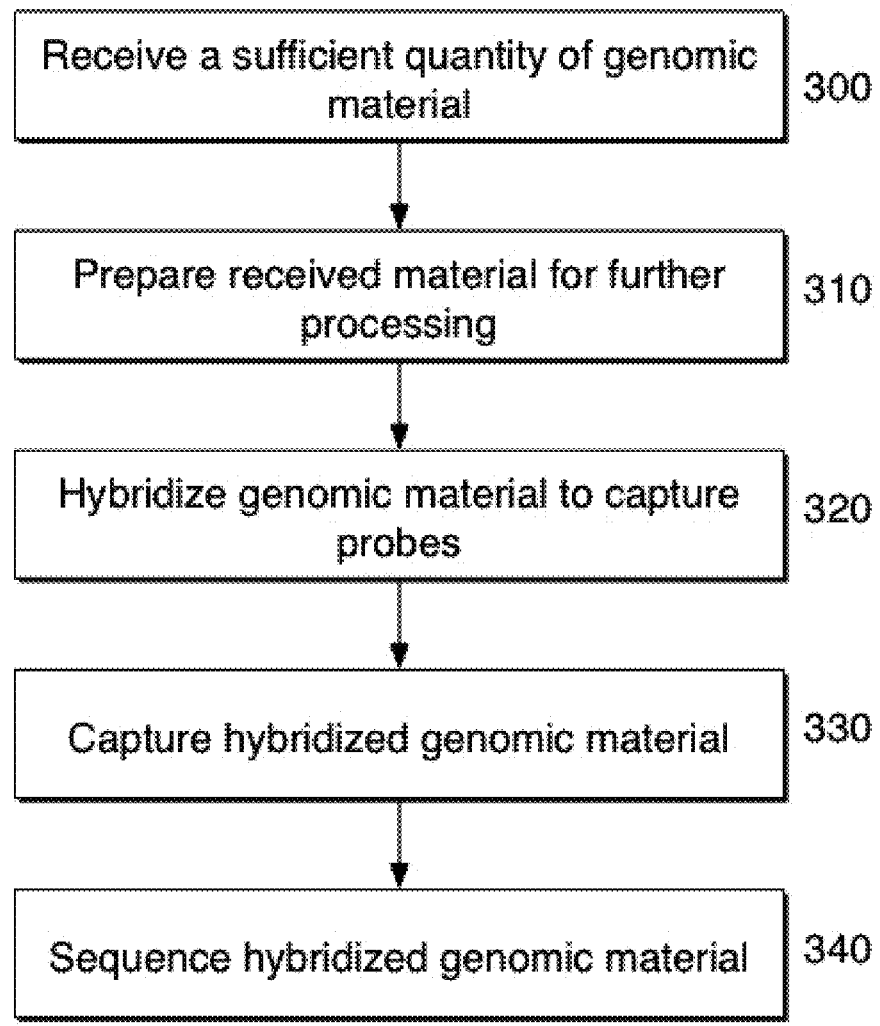
FIG. 3A sets forth a flowchart illustrating the steps of the disclosed sequence capture methods, and in particular where no amplification steps are performed prior to sequencing.
Figure 3B:
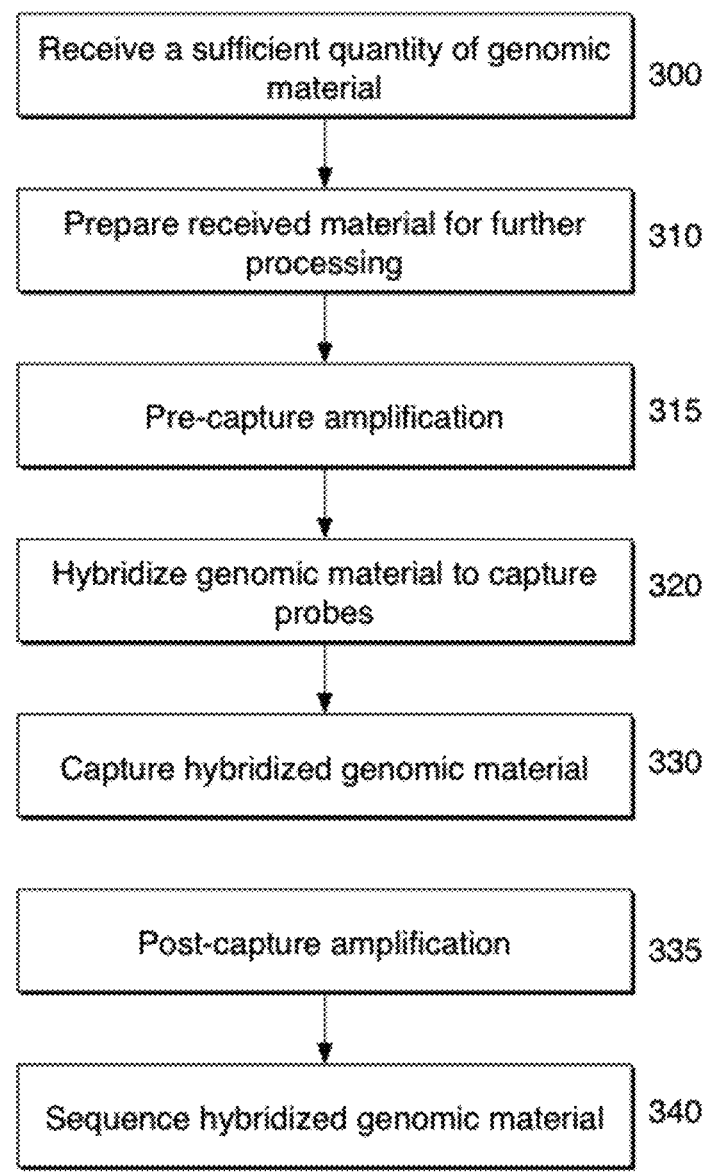
FIG. 3B sets forth a flowchart illustrating the steps of the disclosed sequence capture methods, and in particular where optional amplification steps may be performed prior to sequencing.

With reference to FIGS. 3A and 3B, a first step according to the sequencing method of the present disclosure is to receive genomic material (300), such as from an input sample, as set forth above. In some embodiments, the present disclosure provides a sequencing workflow where an input sample comprising a sufficient amount of genomic material is provided such that that number of amplification cycles prior to sequencing are minimized. In some embodiments, the "sufficient amount" of material is an amount that allows for the sequencing workflow to proceed without any pre-capture amplification cycles. In other embodiments, the "sufficient amount" of material is an amount that allows for the sequencing workflow to proceed with 1 or 2 pre-capture amplification cycles. In yet other embodiments, the "sufficient amount" of material is an amount that allows for the sequencing workflow to proceed with no pre-capture amplification cycles and only a minimal number of post-capture amplification cycles prior to sequencing. In yet other embodiments, the "sufficient amount" of material is an amount that allows for the sequencing workflow to proceed with no pre-capture amplification cycles and between about 1 and about 4 post-amplification cycles prior to sequencing. In further embodiments, the "sufficient amount" of material is an amount that allows for the sequencing workflow to proceed with no pre-capture amplification cycles and between about 1 and about 2 post-amplification cycles prior to sequencing. In some embodiments, the "sufficient amount" of material is an amount that allows for the sequencing workflow to proceed with no pre-capture amplification cycles and no post-capture amplification cycles.

In some embodiments, a quantity of any input sample is at least about 0.5 micrograms. In other embodiments, the quantity of input sample is at least about 1 microgram. In other embodiments, the quantity of input sample is at least about 2.5 micrograms. In other embodiments, the quantity of input sample is at least about 5 micrograms. In other embodiments, the quantity of input sample is at least about 7.5 micrograms. In some embodiments, the quantity of input sample is at least about 9 micrograms. In some embodiments, the quantity of input sample is at least about 10 micrograms. In other embodiments, the quantity of input sample is at least about 50 micrograms. In yet other embodiments, the quantity of the input sample ranges from about 10 micrograms to about 100 micrograms. In yet other embodiments, the quantity of the input sample ranges from about 10 micrograms to about 250 micrograms. In further embodiments, the quantity of the input sample ranges from about 100 micrograms to about 250 micrograms.

In some embodiments, the quantity of genomic material within the input sample for use with the disclosed methods is at least 5 times greater than a quantity of material within an input sample for use with traditional sequence capture methods. In some embodiments, the quantity of genomic material within the input sample for use with the disclosed methods is at least 10 times greater than a quantity of material within an input sample for use with traditional sequence capture methods. In some embodiments, the quantity of genomic material within the input sample for use with the disclosed methods is at least 100 times greater than a quantity of material within an input sample for use with traditional sequence capture methods. In some embodiments, the quantity of genomic material within the input sample for use with the disclosed methods is at least 250 times greater than a quantity of material within an input sample for use with traditional sequence capture methods. In some embodiments, the quantity of genomic material within the input sample for use with the disclosed methods is at least 500 times greater than a quantity of material within an input sample for use with traditional sequence capture methods. In some embodiments, the quantity of genomic material within the input sample for use with the disclosed methods is at least 1000 times greater than a quantity of material within an input sample for use with traditional sequence capture methods. In some embodiments, the quantity of genomic material within the input sample for use with the disclosed methods is about 1000 times greater than a quantity of material within an input sample for use with traditional sequence capture methods.

Again with reference to FIGS. 3A and 3B, following receipt of the genomic material (300), the genomic material, comprising target nucleic acid molecules, may be further processed (310). In some embodiments, the genomic material is fragmented, to provide a fragmented genomic sample. In some embodiments, the input sample is fragmented, for example by sonication, or other methods capable of fragmenting nucleic acids. In some embodiments, the input sample is fragmented to an average size of between about 100 bp to about 500 bp. In some embodiments, the input sample is fragmented to an average size of between about 500 bp to about 1,000 bp. In other embodiments, the input sample is fragmented to an average size of between about 1,000 bp to about 10,000 bp.

In some embodiments, fragmentation of the genomic material is followed by repairing or "polishing" the ends of the fragmented genomic material. In order to achieve this, the double stranded target molecules within the genomic material are subjected to, for example, a fill-in reaction with a DNA Polymerase such as T4 DNA polymerase or Klenow polymerase in the presence of dNTPs, which results in blunt ended target molecules. In addition, ends of the fragments are phosphorylated using T4 Polynucleotide kinase and methods known to skilled artisans (for example, see Molecular Cloning: A Laboratory Manual, Eds. Sambrook et al., Cold Spring Harbour Press; incorporated herein by reference in its entirety) to add phosphate groups to the 5' termini of the fragments prior to the ligation of the adaptors. Subsequent ligation of the adaptors (e.g., short double stranded blunt end DNA oligonucleotides with about 3-20 base pairs) onto the polished, phosphorylated target DNA may be performed according to any method which is known in the art, for example by T4 DNA ligase reaction.

In one particular embodiment, a reaction to polish the ends of fragmented genomic material comprises the fragmented genomic material, T4 DNA polymerase, a T4 DNA polymerase reaction mix, and water. In some embodiments, the reaction is allowed to incubate for a period of time (e.g. 20 minutes to 60 minutes). The genomic material is then recovered from the mixture, such as by extracting with phenol/chloroform followed by precipitation with ethanol.

In some embodiments, the fragmented nucleic acid sample (e.g., fragmented genomic DNA, cDNA, etc.) is modified by ligation to adapters on one or both of the 5' and 3' ends. In some embodiments, one type of adaptor molecule (e.g., adaptor molecule A) is ligated that results in a population of fragments with identical terminal sequences at both ends of the fragment. In other embodiments, two types of adaptor molecules, A and B, are used. This results in a population of molecules composed of three different types: (i) fragments having one adaptor (A) at one end and another adaptor (B) at the other end, (ii) fragments having adaptors A at both ends, and (iii) fragments having adaptors B at both ends. In other embodiments, adaptors are constructed in such a way that after they are ligated to the fragmented nucleic acid sample, each individual strand of the nucleic acid fragment will have one adaptor (A) at one end and another adaptor (B) at the other end.

In one particular embodiment, ligation to linkers is accomplished by reacting the fragmented (and end repaired) genomic material with linkers, T4 DNA ligase, a ligation buffer, and water. Genomic material may then be purified and or size-selected by methods known to those of ordinary skill in the art.

Figure 2:
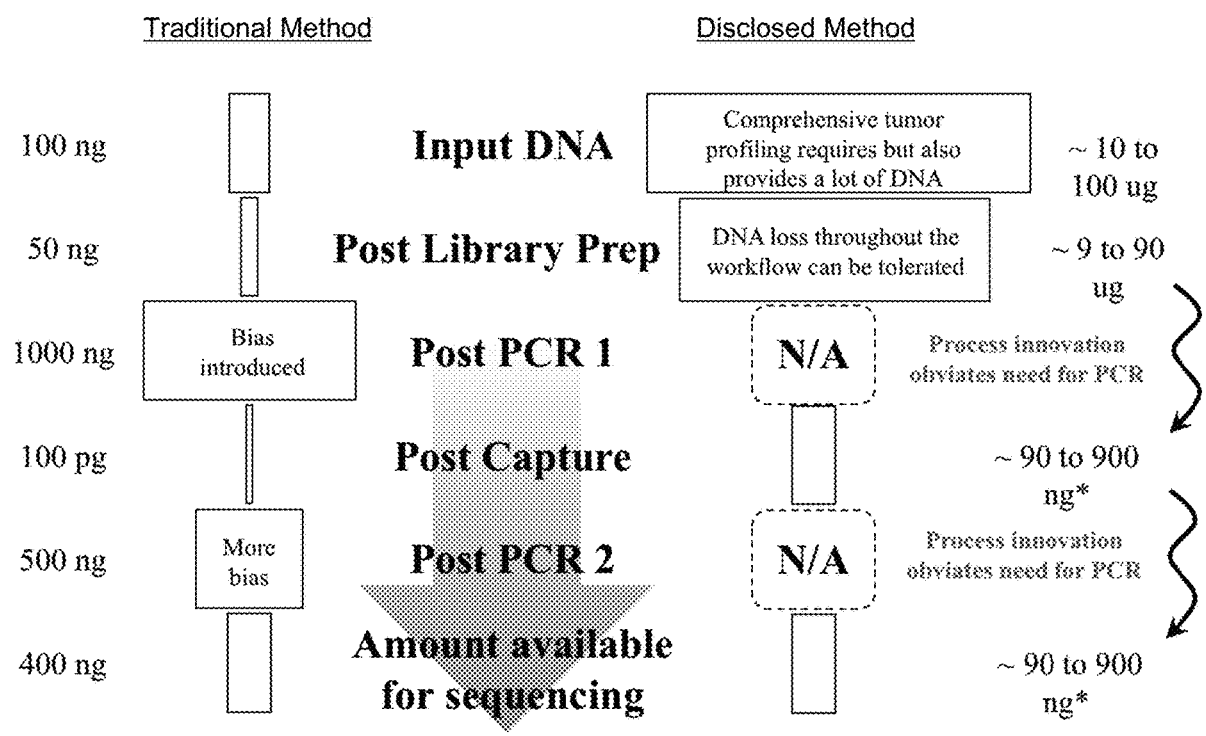
FIG. 2 provides a comparison of a traditional sequence capture method as compared with the disclosed sequence capture method.
Figure 4:
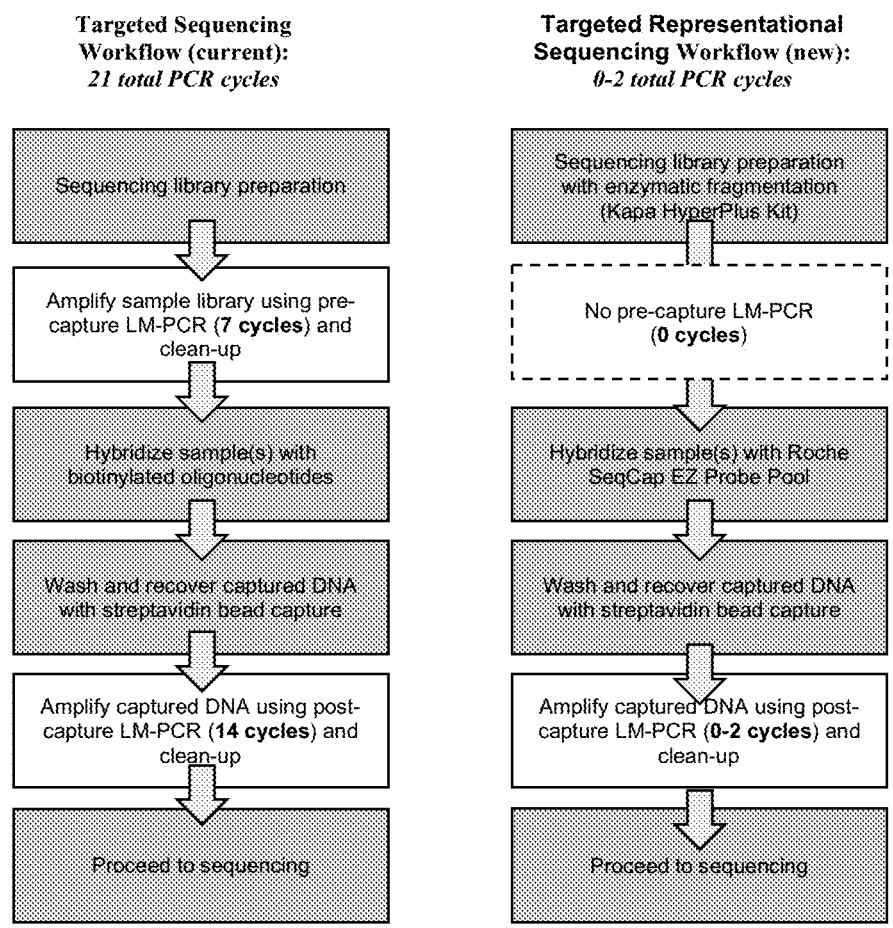
FIG. 4 provides a further comparison of traditional targeted sequencing workflows as compared with the disclosed targeted representational sequencing workflow. Current Targeted Sequencing protocols (left column), such as those relying on hybridization with biotinylated capture oligonucleotides, incorporate numerous cycles of PCR amplification (21 total cycles in this example) to increase sample DNA mass during the workflow. The Targeted Representational Sequencing Workflow (right column) reduces the total amplification during the workflow such as depicted (0-2 amplification cycles) or as described in other embodiments herein. The PCR amplification steps in the workflows are indicated by white boxes.

As compared with traditional sequencing methods, such as depicted in FIGS. 1, 2, and 4, the present methods exploit the higher quantities of genomic material in the input sample such that either no amplification is needed after incorporation of the adapters and prior to hybridization (see, e.g. FIG. 3A), or a minimal number of amplification cycles are needed after incorporation of the adapters and prior to hybridization (see, e.g. FIG. 3B). In some embodiments, an optional pre-capture amplifications step is incorporated, where the pre-capture amplification step comprises from 1 to 3 amplification cycles. In other embodiments, an optional pre-capture amplifications step is incorporated, where the pre-amplification step comprises 1 or 2 amplification cycles. In yet other embodiments, an optional pre-capture amplifications step is incorporated, where the pre-amplification step comprises 1 amplification cycle. In even further embodiments, no amplification cycles are performed pre-capture.

The genomic materials are then denatured to separate complementary DNA strands according to procedures known to those of ordinary skill in the art. The denatured genomic material is then subjected to a hybridization reaction (320), where the hybridization reaction mixture comprises, for example, DNA capture probes complementary in nucleic acid sequence to the target within the genomic material, Cot1 fraction blocking DNA (to block nonspecific hybridization), and blocking oligonucleotides. The DNA capture probes may be biotinylated for subsequent immobilization using streptavidin coated beads or surfaces, or affixed directly to solid supports such as microarrays. Following hybridization (320), non-targeted and unbound nucleic acids are washed from the solid support and the bound, targeted nucleic acids are eluted from the microarray or capture beads or capture surface following protocols known in the art. In some embodiments, the hybridization step 320 utilizes a Roche SeqCap EZ Probe Pool. A Roche SeqCap EZ Probe Pool consists of a mixture of anywhere from tens to millions of different biotinylated single-stranded DNA oligonucleotides in solution, each with a specific sequence, where the length of individual oligonucleotides can range from about 50 nucleotides to about 100 nucleotides with a typical size of about 75 nucleotides. A Roche SeqCap EZ Probe Pool can be used in sequence capture experiments to hybridize to targeted complementary fragments of a DNA sequencing library and thus to capture and enrich them relative to untargeted fragments of the same DNA sequencing library prior to sequencing. The DNA sequencing library may be constructed from genomic DNA for genome analysis, or from cDNA prepared from RNA or mRNA for transcriptome analysis, and it may be constructed from the DNA or cDNA of any species of organism from which these nucleic acids can be extracted.

In some embodiments, hybridization takes place on a solid support. In some embodiments, the solid support comprises beads, whereas the beads are in solution, for example in a tube or other such container, or for example aliquoted into wells of an assay plate (e.g., 12 well, 24 well, 96 well, 384 well, and the like).

In some embodiments, following hybridization of the genomic material with biotinylated DNA capture probes (320), streptavidin coated beads are incubated with the hybridized genomic material such that the hybridized genomic material is immobilized via a streptavidin-biotin bond and any non-targeted genomic material is removed by washing (bead capture, 330) (see FIGS. 3A, 3B, and 4). Captured genomic material is then eluted and provided for sequencing or the captured genomic material is first amplified prior to sequencing.

In some embodiments, and in contrast to the procedure identified in FIG. 1, no further amplification step is performed following elution of the genomic material after bead capture and prior to sequencing. Without wishing to be bound by any particular, by providing a sufficient amount of input genomic material at step 300, an amount of captured material present at steps 330 and/or 340 is of a quantity similar to that provided by traditional sequencing methods where, according those traditional methods, two discrete amplifications steps are needed to increase the amount of genomic material (see the comparison set forth in FIG. 2 and also FIG. 1). It is believed that the process innovations disclosed herein, e.g. preparation of a representative sampling, obviates the need for PCR, provided that a sufficient quantity of material is initially provided, and that a sufficient quantity of material is propagated through each step of the disclosed sequencing method.

Alternatively, a minimal number of amplification cycles (e.g. between 1 and 4 amplification cycles, or between 1 and 3 amplification cycles) are performed post-capture and prior to sequencing (see FIGS. 3B and 4) and such minimal cycles may further increase the amount of material available post-capture so as to provide about the same amount of material as in a traditional sequencing workflow (see FIG. 2). In some embodiments, 1 or 2 amplification cycles are performed post-capture but prior to sequencing. In other embodiments, 1 amplification cycle is performed post-capture but prior to sequencing. In yet other embodiments, 2 amplification cycles are performed post-capture but prior to sequencing.

Where one or more amplification processes or steps (either pre- or post-capture) are incorporated into the workflow of the present disclosure, an aggregate number of amplification cycles, i.e. the sum of pre-capture amplification cycles and post-capture amplification cycles but prior to sequencing, does not exceed 4 cycles. For example, 1 amplification cycle may be performed pre-capture and 2 amplification cycles may be performed post-capture. In other embodiments, the aggregate number of amplification cycles prior to sequencing does not exceed 3 cycles. In yet other embodiments, the aggregate number of amplification cycles prior to sequencing does not exceed 2 cycles. In yet further embodiments, only a single amplification cycle is included in the workflow prior to sequencing.

In some embodiments, target nucleic acids within the genomic material are enriched by hybridizing the target nucleic acid sample against a microarray comprising distributed nucleic acid probes directed to a specific region or specific regions of the genome. After hybridization, target nucleic acid sequences present in the genomic sample are enriched by washing the array and eluting the hybridized genomic nucleic acids from the array. In other embodiments, the present disclosure comprises a method for uniform enrichment of a population of target nucleic acid molecules within the sample of genomic material, comprising providing the target nucleic acid molecules, hybridizing the sample to a support comprising immobilized nucleic acid probes under conditions to support hybridization between the immobilized nucleic acid probes and the plurality of target nucleic acid sequences, wherein said immobilized nucleic acid probes are complementary to said plurality of target nucleic acid sequences, and wherein said immobilized nucleic acid probes provide uniform hybridization among said plurality of target nucleic acid sequences, and separating non-hybridized nucleic acid sequences from hybridized target nucleic acid sequences thereby enriching a population of nucleic acid molecules in the input sample.

Sequencing (340) may be performed according to any method known to those of ordinary skill in the art. In some embodiments, sequencing methods include Sanger sequencing and dye-terminator sequencing, as well as next-generation sequencing technologies such as pyrosequencing, nanopore sequencing, micropore-based sequencing, nanoball sequencing, MPSS, SOLiD, Illumina, Ion Torrent, Starlite, SMRT, tSMS, sequencing by synthesis, sequencing by ligation, mass spectrometry sequencing, polymerase sequencing, RNA polymerase (RNAP) sequencing, microscopy-based sequencing, microfluidic Sanger sequencing, microscopy-based sequencing, RNAP sequencing, tunneling currents DNA sequencing, and in vitro virus sequencing. See WO2014144478, WO2015058093, WO2014106076 and WO2013068528, each of which is hereby incorporated by reference in its entirety.

In some embodiments, sequencing (340) can be performed by a number of different methods, such as by employing sequencing by synthesis technology. Sequencing by synthesis according to the prior art is defined as any sequencing method which monitors the generation of side products upon incorporation of a specific deoxynucleoside-triphosphate during the sequencing reaction (Hyman, 1988, Anal. Biochem. 174:423-436; Rhonaghi et al., 1998, Science 281:363-365). One prominent embodiment of the sequencing by synthesis reaction is the pyrophosphate sequencing method. In this case, generation of pyrophosphate during nucleotide incorporation is monitored by an enzymatic cascade which results in the generation of a chemo-luminescent signal. The 454 Genome Sequencer System (Roche Applied Science cat. No. 04 760 085 001), an example of sequence by synthesis, is based on the pyrophosphate sequencing technology. For sequencing on a 454 GS20 or 454 FLX instrument, the average genomic DNA fragment size is in the range of 200 or 600 bp, respectively, as described in the product literature.

In some embodiments, a sequencing by synthesis reaction can alternatively be based on a terminator dye type of sequencing reaction. In this case, the incorporated dye deoxynucleotriphosphates (ddNTPs) building blocks comprise a detectable label, which is preferably a fluorescent label that prevents further extension of the nascent DNA strand. The label is then removed and detected upon incorporation of the ddNTP building block into the template/primer extension hybrid for example by using a DNA polymerase comprising a 3'-5' exonuclease or proofreading activity.

In some embodiments, and in the case of the Genome Sequencer workflow (Roche Applied Science Catalog No. 04 896 548 001), in a first step, (clonal) amplification is performed by emulsion PCR. Thus, it is also within the scope of the present disclosure, that the step of amplification is performed by emulsion PCR methods. The beads carrying the clonally amplified target nucleic acids may then become arbitrarily transferred into a picotiter plate according to the manufacturer's protocol and subjected to a pyrophosphate sequencing reaction for sequence determination.

In some embodiments, sequencing is performed using a next-generation sequencing method such as that provided by Illumina, Inc. (the "Illumina Sequencing Method"). Without wishing to be bound by any particular theory, the Illumina next-generation sequencing technology uses clonal amplification and sequencing by synthesis (SBS) chemistry to enable rapid, accurate sequencing. The process simultaneously identifies DNA bases while incorporating them into a nucleic acid chain. Each base emits a unique fluorescent signal as it is added to the growing strand, which is used to determine the order of the DNA sequence.

In some embodiments, sequencing is performed using a single-molecule real-time sequencing, such as PacBio available from Pacific Biosciences of California, Inc.

Kits

In one embodiment, the present disclosure provides a kit for performing uniform enrichment of target nucleic acid sequences comprising one or more containers, wherein said one or more containers comprises a solid support comprising immobilized nucleic acid probes, wherein said probes are selected from a group consisting of a plurality of probes hybridizable to a plurality of target nucleic acid sequences and wherein said probes provide for uniform enrichment of said plurality of target nucleic acid sequences, and one or more reagents for performing hybridizations, washes, and elution of target nucleic acid sequences, and wherein a sufficient quantity of each kit component is provided to accommodate and process an input sample comprising at least about 10 micrograms of genomic material.

In another embodiment, the present disclosure provides a kit for performing uniform enrichment of target nucleic acid sequences comprising one or more containers, wherein said one or more containers comprises a solid support comprising immobilized nucleic acid probes, wherein said probes are selected from a group consisting of a plurality of probes hybridizable to a plurality of target nucleic acid sequences and wherein said probes provide for uniform enrichment of said plurality of target nucleic acid sequences, and one or more reagents for performing hybridizations, washes, and elution of target nucleic acid sequences, and wherein a sufficient quantity of each kit component is provided such that the number of amplification cycles performed prior to sequencing are minimized.

In one embodiment, the present disclosure provides a kit for performing uniform enrichment of target nucleic acid sequences comprising one or more containers, wherein said one or more containers comprises biotinylated nucleic acid probes, wherein said probes are selected from a group consisting of a plurality of probes hybridizable to a plurality of target nucleic acid sequences and wherein said probes provide for uniform enrichment of said plurality of target nucleic acid sequences, and one or more reagents for performing hybridizations, washes, and elution of target nucleic acid sequences, and wherein a sufficient quantity of each kit component is provided to accommodate and process an input sample comprising at least about 10 micrograms of genomic material.

In some embodiments, the kits comprise instructions and/or other components for homogenizing a tumor sample or lymph node sample, and/or components for purifying any resulting homogenate. In some embodiments, the kits comprise components for isolating, extracting, and/or purifying genomic material from a homogenate derived from a tumor sample or a lymph node.

In some embodiments, the kits comprise components to stabilize a whole blood sample (e.g. to prevent clotting of blood) or to extract genomic material from a whole blood sample.

In some embodiments, the kits comprise instructions to prepare sequencing libraries from at least about 10 micrograms of genomic material.

In some embodiments, the kits comprise probes and primers such that pre-capture and/or post-capture amplification (e.g. by ligation-mediated PCR) may be performed.

ADDITIONAL EMBODIMENTS

In another aspect of the present disclosure is a method of sequencing genomic material within a sample comprising: homogenizing a tumor sample and/or lymph node sample to provide a homogenized sample; isolating at least 10 micrograms of genomic material from the homogenized sample; preparing the at least 10 micrograms of isolated genomic material for sequencing; and sequencing the prepared genomic material. In some embodiments, the method does not comprise any amplification steps prior to sequencing. In some embodiments, the method comprises at least one pre-capture or post-capture amplification step, wherein an aggregate number of amplification cycles conducted during the at least one pre-capture or post-capture amplification step is at most 4 cycles. In some embodiments, the aggregate number of amplification cycles is 3. In some embodiments, the aggregate number of amplification cycles is 2. In some embodiments, the preparing of the at least 10 micrograms of isolated genomic material for sequencing comprises hybridizing the at least 10 micrograms of isolated genomic to capture probes and capturing the hybridized genomic material. In some embodiments, an amount of captured genomic material ranges from about 90 ng to about 900 ng. In some embodiments, 1 or 2 amplification cycles are performed on the captured genomic material. In some embodiments, the homogenized sample comprises a representative sampling of cells.

In another aspect of the present disclosure is a method of sequencing DNA within a sample comprising isolating at least 10 micrograms of DNA from a blood sample; preparing the at least 10 micrograms of isolated DNA for sequencing, and sequencing the prepared DNA. In some embodiments, the method comprises 0 amplification steps prior to sequencing. In some embodiments, the preparing of the at least 10 micrograms of isolated DNA for sequencing comprises hybridizing the at least 10 micrograms of isolated genomic to capture probes and capturing the hybridized genomic material. In some embodiments, an amount of captured genomic material ranges from about 90 ng to about 900 ng. In some embodiments, 1 or 2 amplification cycles are performed on the captured genomic material.

In another aspect of the present disclosure is a method of targeted representational sequencing comprising: (i) homogenizing at least a portion of a tumor, one or more whole or partial lymph nodes, or any combination thereof to provide a homogenized sample; (ii) extracting genomic material from the homogenized sample; (iii) capturing the extracted genomic material onto beads; and (iv) sequencing the captured genomic material; wherein the targeted representational sequencing comprises performing at most 4 amplification cycles prior to sequencing of the captured genomic material. In some embodiments, the at most 3 amplification cycles may be conducted prior to capture of the extracted genomic material or after capture of the extracted genomic material, or any combination thereof. In some embodiments, no pre-capture amplification cycles are conducted. In some embodiments, an amount of captured genomic material ranges from about 90 ng to about 900 ng. In some embodiments, from 1 to 3 amplification cycles are performed following capture of the extracted genomic material, but prior to sequencing. In some embodiments, at least 9 micrograms of genomic material is extracted from the homogenized sample. In some embodiments, at least 100 times more genomic material is derived from the homogenized sample as compared with an amount of input material used in a sequencing method requiring more than 4 amplification cycles.

In another aspect of the present disclosure is a method of sequencing DNA within a sample comprising: providing at least 10 micrograms of input genomic material, the at least 10 micrograms of genomic material derived from a tumor sample, a lymph node sample, or a blood sample, isolating DNA from the input genomic sample, preparing the isolated DNA for sequencing, and sequencing the prepared DNA, wherein the method does not comprise any amplification steps. In some embodiments, the at least 10 micrograms of input genomic material is derived from multiple histological and/or biopsy specimens. In some embodiments, the at least 10 micrograms of input genomic material is derived from a homogenized tumor sample. In some embodiments, at least 10 micrograms of input genomic material is derived from a homogenized lymph node sample. In some embodiments, at least 10 micrograms of input genomic material is a representative sampling of the tumor sample, lymph node sample, or blood sample from which it is derived. In some embodiments, the sequencing is performed using a next-generation sequencing method. In some embodiments, sequencing is performed using a synthesis sequencing methodology.

In another aspect of the present disclosure is a method of reducing PCR-introduced mutations during sequencing comprising isolating DNA from a sample comprising a sufficient amount of genomic material; preparing the isolated DNA for sequencing; and sequencing the prepared DNA, wherein the method comprises at most 3 amplification cycles prior to sequencing. In some embodiments, the method comprises 1 or 2 amplification cycles prior to sequencing. In some embodiments, sufficient amount of input genomic material is an amount such that no pre-capture amplification cycles are utilized. In some embodiments, the sample is derived from a patient suspected of having cancer. In some embodiments, the sample is derived from a patient diagnosed with cancer. In some embodiments, the sample is derived from a patient at risk of developing cancer. In some embodiments, the sample is derived from healthy tissue samples. In some embodiments, 10 micrograms of DNA is isolated from the sample.

In another aspect of the present disclosure is a sequencing method where PCR-introduced mutations are reduced, the sequencing method comprising capturing at least 0.05 micrograms of genomic material, and performing between 0 and 2 amplification cycles prior to sequencing. In some embodiments, 0 amplification cycles are conducted. In other embodiments, 1 amplification cycle is conducted. In yet other embodiments, 2 amplification cycles are conducted.

In another aspect of the present disclosure is a sequence capture method where PCR-introduced biases in the proportional representation of genome content are reduced, the sequencing method comprising providing an input sample comprising at least 10 micrograms of genomic material, and where the sequence capture method comprises performing between 0 and 2 amplification cycles prior to sequencing. In some embodiments, 0 amplification cycles are conducted. In other embodiments, 1 amplification cycle is conducted. In yet other embodiments, 2 amplification cycles are conducted.

In another aspect of the present disclosure is a sequence capture method where PCR-introduced mutations are eliminated, the sequence capture method comprising preparing an input sample comprising at least 10 micrograms of genomic material.

In another aspect of the present disclosure is a sequence capture method where a step of removing PCR-duplicate reads prior to sequencing is eliminated, the sequence capture method comprising providing an input sample comprising at least 10 micrograms of genomic material.

In another aspect of the present disclosure is a sequencing workflow where an input sample comprising at least 10 micrograms of genomic material is provided and where the workflow comprises performing between 0 and 2 amplification cycles prior to sequencing. In some embodiments, an amount of genomic material ranges from about 10 micrograms to about 1,000 micrograms.

In another aspect of the present disclosure is a sequencing method where PCR-introduced mutations are reduced, the sequencing method comprising preparing a sequencing library having at least 9 micrograms of genomic material. In some embodiments, the method comprises performing between 1 and 3 amplification cycles prior to sequencing, where the amplification cycles may be performed pre-capture, post-capture, or in both pre-capture and post-capture. In some embodiments, the between 1 and 3 amplification cycles are performed post-capture.

In another aspect of the present disclosure is a sequence capture workflow where an input sample comprising at least 10 micrograms of genomic material is provided and where the workflow comprises performing between 1 and 3 amplification cycles prior to sequencing, where the amplification cycles may be performed pre-capture, post-capture, or in any combination thereof. In some embodiments, the between 1 and 3 amplification cycles are performed post-capture. In some embodiments, an amount of genomic material ranges from about 10 micrograms to about 1,000 micrograms. In some embodiments, the input sample comprises about 10 micrograms of material.

In another aspect of the present disclosure is a method of sequencing genomic material comprising homogenizing a whole or partial tumor or lymph node to provide a homogenized sample, capturing genomic material from the homogenized sample, and sequencing the captured genomic material, wherein the method requires at most 4 amplification cycles prior to sequencing. In some embodiments, the method comprises performing 1 or 2 amplification cycles post-capture, but prior to sequencing. In some embodiments, the input sample comprises between about 10 and about 100 micrograms of material. In some embodiments, the input sample comprises at least 10 micrograms of material. In some embodiments, the input sample comprises at least 1.5 million cells.

In another aspect of the present disclosure is a method of sequencing genomic material comprising obtaining a sample of whole blood or a fraction thereof, capturing genomic material from the sample, and sequencing the genomic material, wherein the method requires at most 4 amplification cycles prior to sequencing. In some embodiments, the method comprises performing 1 or 2 amplification cycles post-capture, but prior to sequencing. In some embodiments, the input sample comprises between about 10 and about 100 micrograms of material. In some embodiments, the input sample comprises at least 10 micrograms of material. In some embodiments, the input sample comprises at least 1.5 million cells.

In another aspect of the present disclosure is a PCR-free sequence capture workflow wherein an input sample comprises a sufficient quantity of genomic material. In some embodiments, an input sample comprising at least 10 micrograms of genomic material is provided and where no amplification processes are required prior to sequencing. In some embodiments, an amount of genomic material ranges from about 10 micrograms to about 1,000 micrograms.

In another aspect of the present disclosure is a PCR-free sequence capture workflow wherein the input sample is at least 5 times greater than a quantity of material within an input sample for use with traditional sequence capture methods.

In another aspect of the present disclosure is a method of sequencing genomic material comprising homogenizing a whole or partial tumor or lymph node to provide a homogenized sample, capturing genomic material from the homogenized sample, and sequencing the captured genomic material, wherein the method does not require amplification of the genomic material prior to sequencing. In some embodiments, the input sample comprises at least 10 micrograms of material. In some embodiments, the input sample comprises at least 1.5 million cells.

In another aspect of the present disclosure is a method of sequencing genomic material comprising obtaining a sample of whole blood or a fraction thereof to provide an input sample, capturing genomic material from the input sample, and sequencing the genomic material, wherein the method does not require amplification of the genomic material prior to sequencing. In some embodiments, the input sample comprises at least 10 micrograms of material. In some embodiments, the input sample comprises at least 1.5 million cells.

In another aspect of the present disclosure is a method of sequencing genomic material comprising obtaining a sufficient quantity of an input sample comprising genomic material, preparing the genomic material for hybridization, hybridizing the prepared genomic material to capture probes, capturing the genomic material from the input sample, and sequencing the genomic material, wherein the method does not require amplification of the genomic material at any stage of the workflow, except where some special form of amplification (e.g. bridge PCR on an Illumina flowcell, emulsion PCR in Ion Torrent sequencing) is performed within the sequencing instrument or as part of the sequencing workflow after sequence capture is completed. In some embodiments, at least about 10 micrograms of genomic material are provided for hybridization.

In another aspect of the present disclosure is a method of treating cancer by identifying cancer subtypes responsive to a particular treatment or active pharmaceutical ingredient, wherein the cancer subtype is identified by sequencing an input sample comprising a representative sampling of a tumor, lymph node, or blood. In some embodiments, the treatment is a targeted treatment, e.g. an antibody-based treatment. In some embodiments, the treatment comprises chemotherapy with one or more active pharmaceutical ingredients.

Additional Embodiment 1

A method of sequencing genomic material within a sample comprising: homogenizing a tumor sample and/or lymph node sample to provide a homogenized sample; isolating at least 0.5 micrograms of genomic material from the homogenized sample; preparing the at least 0.5 micrograms of isolated genomic material for sequencing; and sequencing the prepared genomic material.

Additional Embodiment 2

The method of additional embodiment 1, wherein the method does not comprise any amplification steps prior to sequencing.

Additional Embodiment 3

The method of additional embodiment 1, wherein the method comprises at least one pre-capture or post-capture amplification step, wherein an aggregate number of amplification cycles conducted during the at least one pre-capture or post-capture amplification step is at most 4 cycles.

Additional Embodiment 4

The method of additional embodiment 3, wherein the aggregate number of amplification cycles is 3.

Additional Embodiment 5

The method of additional embodiment 3, wherein the aggregate number of amplification cycles is 2.

Additional Embodiment 6

The method of additional embodiment 1, wherein the preparing of the at least 0.5 micrograms of isolated genomic material for sequencing comprises hybridizing the at least 0.5 micrograms of isolated genomic to capture probes and capturing the hybridized genomic material.

Additional Embodiment 7

The method of additional embodiment 6, wherein an amount of captured genomic material ranges from about 90 ng to about 900 ng.

Additional Embodiment 8

The method of additional embodiment 6, wherein 1 or 2 amplification cycles are performed on the captured genomic material.

Additional Embodiment 9

The method of additional embodiment 1, wherein the homogenized sample comprises a representative sampling of cells.

Additional Embodiment 10

The method of additional embodiment 1, wherein at least 1 microgram of genomic material is isolated from the homogenized sample.

Additional Embodiment 11

The method of additional embodiment 1, wherein at least 5 micrograms of genomic material is isolated from the homogenized sample.

Additional Embodiment 12

The method of additional embodiment 1, wherein at least 10 micrograms of genomic material is isolated from the homogenized sample.

Additional Embodiment 13

A method of sequencing DNA within a sample comprising isolating at least 0.5 micrograms of DNA from a blood sample; preparing the at least 0.5 micrograms of isolated DNA for sequencing; and sequencing the prepared DNA.

Additional Embodiment 14

The method of additional embodiment 13, wherein the method comprises 0 amplification steps prior to sequencing.

Additional Embodiment 15

The method of additional embodiment 13, wherein the preparing of the at least 0.5 micrograms of isolated DNA for sequencing comprises hybridizing the at least 0.5 micrograms of isolated genomic to capture probes and capturing the hybridized genomic material.

Additional Embodiment 16

The method of additional embodiment 15, wherein an amount of captured genomic material ranges from about 90 ng to about 900 ng.

Additional Embodiment 17

The method of additional embodiment 15, wherein 1 or 2 amplification cycles are performed on the captured genomic material.

Additional Embodiment 18

The method of additional embodiment 13, wherein at least 1 microgram of DNA is isolated from the blood sample.

Additional Embodiment 19

A method of targeted representational sequencing comprising: (i) homogenizing at least a portion of a tumor, one or more whole or partial lymph nodes, or any combination thereof to provide a homogenized sample; (ii) extracting genomic material from the homogenized sample; (iii) capturing the extracted genomic material onto beads; and (iv) sequencing the captured genomic material; wherein the targeted representational sequencing comprises performing at most 4 amplification cycles prior to sequencing of the captured genomic material.

Additional Embodiment 20

The method of additional embodiment 19, wherein the at most 4 amplification cycles may be conducted prior to capture of the extracted genomic material or after capture of the extracted genomic material, or any combination thereof.

Additional Embodiment 21

The method of additional embodiment 19, wherein no pre-capture amplification cycles are conducted.

Additional Embodiment 22

The method of additional embodiment 21, wherein an amount of captured genomic material ranges from about 90 ng to about 900 ng.

Additional Embodiment 23

The method of additional embodiment 19, wherein from 1 to 3 amplification cycles are performed following capture of the extracted genomic material, but prior to sequencing.

Additional Embodiment 24

The method of additional embodiment 19, wherein at least 1 microgram of genomic material is extracted from the homogenized sample.

Additional Embodiment 25

The method of additional embodiment 19, wherein at least 100 times more genomic material is derived from the homogenized sample as compared with an amount of input material used in a sequencing method requiring more than 4 amplification cycles.

Additional Embodiment 26

A method of sequencing DNA within a sample comprising: isolating at least 0.5 micrograms of genomic material from an input sample, the input sample derived from a tumor sample, a lymph node sample, a blood sample or any combination thereof; preparing the isolated genomic material for sequencing; and sequencing the prepared genomic material, wherein the method does not comprise any amplification steps.

Additional Embodiment 27

The method of additional embodiment 26, wherein the at least 0.5 micrograms of genomic material is derived from multiple histological and/or biopsy specimens.

Additional Embodiment 28

The method of additional embodiment 26, wherein the at least 0.5 micrograms of genomic material is derived from a homogenized tumor sample.

Additional Embodiment 29

The method of additional embodiment 26, wherein the at least 0.5 micrograms of genomic material is derived from a homogenized lymph node sample.

Additional Embodiment 30

The method of additional embodiment 26, wherein the at least 0.5 micrograms of genomic material is a representative sampling of the tumor sample, lymph node sample, or blood sample from which it is derived.

Additional Embodiment 31

The method of additional embodiment 26, wherein the sequencing is performed using a next-generation sequencing method.

Additional Embodiment 32

The method of additional embodiment 26, wherein the sequencing is performed using a synthesis sequencing methodology.

Additional Embodiment 33

A method of reducing PCR-introduced mutations during sequencing comprising isolating DNA from a sample comprising a sufficient amount of genomic material; preparing the isolated DNA for sequencing; and sequencing the prepared DNA, wherein the method comprises at most 3 amplification cycles prior to sequencing.

Additional Embodiment 34

The method of additional embodiment 33, wherein the method comprises 1 or 2 amplification cycles prior to sequencing.

Additional Embodiment 35

The method of additional embodiment 33, wherein the sufficient amount of input genomic material is an amount such that no pre-capture amplification cycles are utilized.

Additional Embodiment 36

The method of additional embodiment 33, wherein the sample is derived from a patient suspected of having cancer.

Additional Embodiment 37

The method of additional embodiment 33, wherein the sample is derived from a patient diagnosed with cancer.

Additional Embodiment 38

The method of additional embodiment 33, wherein the sample is derived from a patient at risk of developing cancer.

Additional Embodiment 39

The method of additional embodiment 33, wherein the sample is derived from healthy tissue samples.

Additional Embodiment 40

The method of additional embodiment 33, wherein about 0.5 micrograms of DNA is isolated from the sample.

Additional Embodiment 41

The method of additional embodiment 33, wherein at least 0.5 micrograms of DNA is isolated from the sample.

Additional Embodiment 42

A method of treating cancer by identifying cancer subtypes responsive to a particular treatment or active pharmaceutical ingredient, wherein the cancer subtype is identified by sequencing an input sample comprising a representative sampling of a tumor, lymph node, or blood, the input sample comprising a sufficient quantity of genomic material, and wherein at most 4 amplification cycles are conducted prior to sequencing.

Additional Embodiment 43

The method of additional embodiment 42, wherein at most 3 amplification cycles are conducted prior to sequencing.

Additional Embodiment 44

The method of additional embodiment 42, wherein at most 2 amplification cycles are conducted prior to sequencing.

Additional Embodiment 45

The method of additional embodiment 42, wherein at most 1 amplification cycle is conducted prior to sequencing.

Additional Embodiment 46

The method of additional embodiment 42, wherein 0 amplification cycles are conducted prior to sequencing.

Additional Embodiment 47

The method of additional embodiment 42, wherein the quantity of genomic material is at least 0.5 micrograms.

Additional Embodiment 48

The method of additional embodiment 42, wherein the quantity of genomic material is at least 1 microgram.

Additional Embodiment 49

The method of additional embodiment 42, wherein the quantity of genomic material is at least 5 micrograms.

Additional Embodiment 50

The method of additional embodiment 42, wherein the quantity of genomic material is at least 10 micrograms.

EXAMPLES

Protocol for Targeted Representational Sequencing

Examples 1 through 5 set forth a protocol for targeted representational sequencing. The examples may refer to certain laboratory equipment and/or consumables. Examples of such equipment and consumables are set forth in Tables 1 and 2, along with the suppler and catalog number, where appropriate. In accordance with the methods described herein, the skilled artisan will appreciate that the steps recited at Example 4 are optional. The skilled artisan will appreciate that the protocol described herein may be adjusted to accommodate input amounts of genomic DNA lesser or greater than those described. The skilled artisan will also appreciate that an additional pre-capture amplification step may be incorporated into this protocol, although such a pre-capture amplification step is optional as noted herein.

TABLE 1

Laboratory equipment referred to within Examples 1 through 5.

| Equipment | Supplier | Catalog No. |
| --- | --- | --- |
| DNA Vacuum Concentrator (1.5 ml tubes) (optional) | Multiple Vendors | |
| Covaris Ultra Sonicator (optional) | Covaris | Multiple models (e.g. S220, E220) |
| DynaMag-2 Magnet (16 × 0.2 ml tube holder) (optional) | Thermo Fisher | 12321D |
| DynaMag-96 Side Magnet | Thermo Fisher | 12331D |
| Microcentrifuge (16,000 × g capability) | Multiple Vendors | |
| Spectrophotometer | NanoDrop | ND-1000 |
| Bioanalyzer 2100 | Agilent | |
| Thermocycler (capable of maintaining +47° C. for 16-20 hours; programmable heated lid recommended) | Multiple Vendors | |
| Vortex mixer | Multiple Vendors | |

TABLE 2

Consumables referred to within Examples 1 through 5.

| Component | Supplier | Package Size | Catalog No. |
| --- | --- | --- | --- |
| SeqCap Adapter Kit A 96 | Roche | 96 reactions | 07 141 530 001 |
| SeqCap EZ Reagent Kit Plus v2 | Roche | 24 reactions | 06 953 247 001 |
| KAPA HyperPlus Library Preparation Kit | Roche | 24 reactions | 07 962 401 001 |
| Agencourt AMPure XP Reagent | Beckman Coulter | 5 ml | A63880 |
| Agilent DNA 1000 Kit | Agilent | 1 kit | 5067-1504 |
| Elution buffer (10 mM Tris-HCl, pH 8.0) | Multiple Vendors | | |
| Ethanol (absolute), for molecular biology | Sigma-Aldrich | 500 ml | E7023-500ML |
| PCR tubes (0.2 ml) | Multiple Vendors | | |
| Microcentrifuge tubes (1.5 ml) | Multiple Vendors | | |
| Water, PCR Grade | Sigma-Aldrich | 4 × 25 ml | 3315843001 |

Example 1—Sample Library Preparation Using KAPA HyperPlus Library Preparation 1.1. Resuspend the lyophilized Index Adapters (Adapter Kit A).

1.1.1. Spin the lyophilized index adapters, contained in the SeqCap Adapter Kit A and/or B, briefly to allow the contents to pellet at the bottom of the tube.

1.1.2. Add 50 microliters cold, PCR-grade water to each of the 12 tubes labeled 'SeqCap Index Adapter' in the SeqCap Adapter Kit A and/or B. Keep adapters on ice.

1.1.3. Briefly vortex the index adapters plus PCR-grade water and spin down the resuspended index adapter tubes.

1.1.4. The tubes of resuspended index adapters should be stored at −15 to −25° C.

1.2. Prepare the Sample Library 1.2.1. Dilute gDNA (about 100 ng to about 1 microgram) to be used for library construction in 10 mM Tris-HCl (pH 8.0) to total volume of 35 microliters into a 0.2 ml tube or well of PCR plate.

1.2.2. Assemble each fragmentation reaction on ice by adding the components in the order shown:

| Component | Volume |
|---|---|
| 100 ng gDNA | 35 μl |
| KAPA Frag Buffer (10x) | 5 μl |
| KAPA Frag Enzyme | 10 μl |
| Total | 50 μl |

1.2.3. Mix Fragmentation Reaction thoroughly.

1.2.4. Place in a pre-cooled thermocycler, set to instant incubate at 4° C. Then incubate the samples using the program outlined below:

1.2.4.1. Step 1: 20 minutes at +37° C.

1.2.4.2. Step 2: Hold at +4° C.

1.2.5. Transfer reaction to ice and proceed immediately to the next step.

1.2.6. Perform End Repair and A-tailing Reaction as follows:

1.2.6.1. Prepare a master mix of the following reagents:

| End Repair Master Mix | Per Individual Sample Library |
|---|---|
| KAPA End Repair & A-Tailing Buffer | 7 μl |
| KAPA End Repair & A-Tailing Enzyme Mix | 3 μl |
| Total | 10 μl |

1.2.6.2. To each 50 microliters fragmented sample add 10 microliters of End Repair and A-tailing Master Mix.

1.2.6.3. Mix the End Repair and A-tailing reaction thoroughly.

1.2.6.4. Place on ice and immediately proceed to next step.

1.2.6.5. Perform the End Repair and A-Tailing incubation in a thermocycler using the following program with heated lid:

1.2.6.5.1. Step 1: 30 minutes at +65° C.

1.2.6.5.2. Step 2: Hold at +4° C.

1.2.6.6. Following the 30-minute incubation, proceed immediately to the next step.

1.2.7. Proceed with the Adapter Ligation Reaction Setup:

1.2.7.1. Prepare a master mix of the following reagents:

| Ligation Master Mix | Per Individual Sample Library |
|---|---|
| PCR-grade water | 5 μl |
| KAPA Ligation Buffer | 30 μl |
| KAPA DNA Ligase | 10 μl |
| Total | 45 μl |

1.2.7.2. Add 5 ul of the SeqCap Library Adapter (with the desired Index) to the sample well containing the End Repair and A-tailing mix plus DNA. Ensure that you record the index used for each sample.

1.2.7.3. To each sample well that contains 65 microliters End Repair and A-tailing mix/DNA/adapter, add 45 microliters of the Ligation Master Mix, resulting in a total volume of 110 microliters.

1.2.7.4. Mix the Ligation reaction thoroughly.

1.2.7.5. Incubate the Ligation reaction at +20° C. for 15 minutes.

1.2.7.6. Following the incubation, proceed immediately to the next step.

1.2.8. Perform the Post-Ligation Cleanup as follows:

1.2.8.1. To each Ligation Reaction, add 88 microliters room temperature AMPure XP Reagent that has been thoroughly resuspended.

| First Post Ligation Cleanup | Per Individual Sample Library |
|---|---|
| Ligation Reaction | 110 μl |
| AMPure XP Reagent | 88 μl |
| Total | 198 μl |

1.2.8.2. Mix the Ligation Reaction product and AMPure XP Reagent thoroughly.

1.2.8.3. Incubate the samples at room temperature for 5 minutes to allow the DNA to bind to the beads.

1.2.8.4. Place the samples in a magnetic particle collector to capture the beads. Incubate until the liquid is clear.

1.2.8.5. Carefully remove and discard the supernatant.

1.2.8.6. Keeping the samples on the magnetic particle collector, add 200 microliters of freshly-prepared 80% ethanol.

1.2.8.7. Incubate the samples at room temperature for ≥30 seconds.

1.2.8.8. Carefully remove and discard the ethanol.

1.2.8.9. Keeping the samples on the magnetic particle collector, add 200 microliters of freshly-prepared 80% ethanol.

1.2.8.10. Incubate the samples at room temperature for ≥30 seconds.

1.2.8.11. Carefully remove and discard the ethanol. Try to remove all residual ethanol without disturbing the beads.

1.2.8.12. Allow the beads to dry at room temperature, sufficiently for all the ethanol to evaporate.

1.2.8.13. Remove the samples from the magnetic particle collector.

1.2.8.14. Thoroughly resuspend the beads in 53 microliters of elution buffer (10 mM Tris-HCl, pH 8.0).

1.2.8.15. Incubate the samples at room temperature for 2 minutes to allow the DNA to elute off the beads.

1.2.8.16. Place the samples on a magnetic particle collector to capture the beads. Incubate until the liquid is clear.

1.2.8.17. Transfer 50 microliters supernatant to a fresh tube/well.

Example 2—Hybridize the Sample and SeqCap EZ Probe Pool 2.1.1. Allow the AMPure XP reagent to warm to room temperature for at least 30 minutes before use.

2.1.2. Add 5 microliters of COT Human DNA (1 mg/ml), contained in the SeqCap EZ Accessory Kit v2, to a new tube/well.

2.1.3. Add 3 μg of DNA Sample Library to the sample containing 5 microliters of COT Human DNA. Multiple libraries constructed from the same sample may be pooled for this purpose.

2.1.4. Add 2,000 pmol (or 2 microliters) of the Hybridization Enhancing Oligo (1 microliters of 1,000 pmol SeqCap HE Universal Oligo and 1 microliters of the 1,000 pmol SeqCap HE Index Oligo matching the Sample Library Adapter Index) to the DNA Sample Library plus COT Human DNA.

2.1.5. Determine the total volume of the above mixture by adding input volumes of COT Human DNA, DNA Sample Library Pool, SeqCap HE Universal Oligo and SeqCap HE Index Oligo pool.

2.1.6. Add 2 volumes of AMPure XP Reagent (equilibrated to room temperature and fully resuspended) to the above mixture. Mix thoroughly.

2.1.7. Let the sample incubate at room temperature for 10 minutes to allow the sample library to bind to the beads.

2.1.8. Place the samples on the magnetic particle collector to capture the beads. Allow the solution to clear.

2.1.9. Once clear, remove and discard the supernatant being careful not to disturb the beads.

2.1.10. Add 190 microliters 80% ethanol to the samples containing the bead-bound DNA samples. The samples should be left on the magnetic particle collector during this step.

2.1.11. Incubate at room temperature for ≥30 seconds.

2.1.12. Carefully remove and discard the 80% ethanol. Try to remove all residual ethanol without disturbing the beads.

2.1.13. Allow the beads to dry at room temperature with the tube lid open for 5 minutes (or until dry).

2.1.14. Prepare a master mix of the following reagents, scaling up to reflect number of captures:

2.1.14.1.7.5 microliters of 2× Hybridization Buffer (vial 5)

2.1.14.2.3 microliters of Hybridization Component A (vial 6)

2.1.15. Add 10.5 microliters of the Hybridization Buffer/Hybridization Component A mix from previous step to the bead-bound DNA samples.

2.1.16. Remove samples from the magnetic particle collector and mix thoroughly. It is important that enough mixing is performed at this step to yield a homogeneous mixture.

2.1.17. Let sit at room temperature for 2 minutes.

2.1.18. Place samples on a magnetic particle collector.

2.1.19. After liquid clears, remove 10.5 microliters of supernatant (entire volume) and place in a new tube/well containing 4.5 ul of the SeqCap EZ probe pool. Mix thoroughly.

2.1.20. Perform the hybridization incubation in a thermocycler using the following program with heated lid set to 10° C. above block temperature:

2.1.20.1.95° C. for 5 minutes 2.1.20.2.47° C. for 16-20 hours 2.1.21. For incubation at 47° C. for 16-20 hours, it is important that the thermocycler's heated lid is turned on and set to maintain 10° C. above the hybridization temperature (+57° C.). The sample must remain at 47° C. until it is transferred to the capture beads in step 3.3.

Example 3—Wash and Recover the Captured DNA Sample Library 3.1. Dilute 10× Wash Buffers (I, II, III and Stringent) and 2.5× Bead Wash Buffer, contained in the SeqCap Hybridization and Wash Kit, to create 1× working solutions. Volumes listed below are sufficient for one capture.

| Concentrated Buffer | Volume of Concentrated Buffer | Volume of PCR-grade Water | Total Volume of 1X Buffer* |
| --- | --- | --- | --- |
| 10X Stringent Wash Buffer (vial 4) | 40 μl | 360 μl | 400 μl |
| 10X Wash Buffer I (vial 1) | 30 μl | 270 μl | 300 μl |
| 10X Wash Buffer II (vial 2) | 20 μl | 180 μl | 200 μl |
| 10X Wash Buffer III (vial 3) | 20 μl | 180 μl | 200 μl |
| 2.5X Bead Wash Buffer (vial 7) | 200 μl | 300 μl | 500 μl |

3.2. Prepare the Capture Beads 3.2.1. Allow the Capture Beads, contained in the SeqCap Pure Capture Bead Kit, to equilibrate to room temperature for 30 minutes prior to use.

3.2.2. Vortex the capture beads for 15 seconds before use to ensure a homogeneous mixture of beads.

3.2.3. Aliquot 50 microliters of beads for each capture into a 0.2 ml or 1.5 ml tube (i.e. for one capture use 50 microliters beads and for four captures use 200 microliters beads, etc.). Enough beads for two captures and twelve captures can be prepared in a single 0.2 ml tube and 1.5 ml tube, respectively.

3.2.4. Place the tubes on a magnetic particle collector. Allow the solution to clear (should take less than 5 minutes).

3.2.5. Remove and discard the supernatant being careful not to disturb the beads. Any remaining traces of liquid will be removed with subsequent wash steps.

3.2.6. While the tubes are on the magnetic particle collector, add twice the initial volume of beads of 1× Bead Wash Buffer (i.e. for one capture use 100 microliters of buffer and for four captures use 400 microliters buffer, etc.).

3.2.7. Remove tubes from the magnetic particle collector and mix thoroughly by vortexing or pipetting up and down.

3.2.8. Place the tubes back on the magnetic particle collector to bind the beads.

3.2.9. Once clear, remove and discard the liquid.

3.2.10. Repeat Steps 2.6-2.9 for a total of two washes.

3.2.11. After removing the buffer following the second wash, add 1× the initial volume of beads of 1× Bead Wash Buffer (i.e. 50 microliters buffer per capture).

3.2.12. Remove tubes from magnetic particle collector and mix thoroughly.

3.2.13. Aliquot 50 microliters of resuspended beads into new tube/well for each capture.

3.2.14. Place the tubes on magnetic particle collector to bind the beads. Allow the solution to clear.

3.2.15. Once clear, remove and discard the supernatant.

3.2.16. The Capture Beads are now ready to bind the captured DNA. Proceed immediately to the next step.

3.3. Bind DNA to the Capture Beads 3.3.1. Transfer one hybridization sample to a single prepared tube/well of Capture Beads from the previous step.

3.3.2. Mix thoroughly.

3.3.3. Bind the captured sample to the beads by placing the samples in a thermocycler set to +47° C. for 15 minutes (heated lid set to +57° C.).

3.4. Wash the Capture Beads Plus Bead-Bound DNA 3.4.1. After the 15-minute incubation, remove the samples from the thermocycler.

3.4.2. Thermocycler should remain at 47° C. (heated lid turned on and set to maintain +57° C.) for following steps.

3.4.3. Add 100 microliters of 1× Wash Buffer I to the 15 microliters of Capture Beads plus bead-bound DNA.

3.4.4. Mix thoroughly.

3.4.5. Place the samples on a magnetic particle collector to capture the beads. Allow the solution to clear.

3.4.6. Once clear, remove and discard the supernatant being careful not to disturb the beads.

3.4.7. Add 200 microliters of 1× Stringent Wash Buffer to each sample.

3.4.8. Remove the samples from the magnetic particle collector.

3.4.9. Mix to homogeneity by pipetting up and down.

3.4.10. Place on thermocycler pre-heated to +47° C., close lid (set to +57° C.) and incubate for 5 minutes.

3.4.11. After incubating 5 minutes, remove the sample from thermocycler and place on a magnetic particle collector to capture the beads. Allow the solution to clear.

3.4.12. Once clear, remove and discard the supernatant being careful not to disturb the beads 3.4.13. Repeat Steps 4.6-4.11 for a total of two washes using 1× Stringent Wash Buffer.

3.4.14. Add 200 microliters of room temperature 1× Wash Buffer I.

3.4.15. Mix thoroughly by vortexing for 10 seconds or pipetting up and down 10 times. Ensure that the mixture is homogeneous.

3.4.16. Incubate at room temperature for 1 minute.

3.4.17. Place the samples on a magnetic particle collector to capture the beads. Allow the solution to clear.

3.4.18. Once clear, remove and discard the supernatant being careful not to disturb the beads.

3.4.19. Add 200 microliters of room temperature 1× Wash Buffer II.

3.4.20. Mix thoroughly by vortexing for 10 seconds or pipetting up and down 10 times. Ensure that the mixture is homogeneous.

3.4.21. Incubate at room temperature for 1 minute.

3.4.22. Place the samples on a magnetic particle collector to capture the beads. Allow the solution to clear.

3.4.23. Once clear, remove and discard the supernatant being careful not to disturb the beads.

3.4.24. Add 200 microliters of room temperature 1× Wash Buffer III.

3.4.25. Mix thoroughly by vortexing for 10 seconds or pipetting up and down 10 times. Ensure that the mixture is homogeneous.

3.4.26. Incubate at room temperature for 1 minute.

3.4.27. Place the samples on a magnetic particle collector to capture the beads. Allow the solution to clear.

3.4.28. Once clear, remove and discard the supernatant being careful not to disturb the beads.

3.4.29. Remove the samples from the magnetic particle collector.

3.4.30. Add 15 microliters PCR-grade water to each tube/plate well of bead-bound DNA sample.

Example 4—Amplify the Captured Sample Library Using Pre-Capture Ligation-Mediated PCR (LM-PCR)

4.1. Resuspend the Post-LM-PCR Oligos 4.1.1. Briefly spin the lyophilized Post-LM-PCR Oligos 1 & 2, contained in the SeqCap EZ Accessory Kit v2, to allow the contents to pellet at the bottom of the tube. Please note that both oligos are contained within a single tube.

4.1.2. Add 480 microliters PCR-grade water to the tube of centrifuged oligos.

4.1.3. Briefly vortex the resuspended oligos.

4.1.4. Spin down the tube to collect the contents.

4.1.5. The resuspended oligo tube should be stored at −15 to −25° C.

4.2. Prepare the Post-Capture LM-PCR Master Mix 4.2.1. Prepare a master mix of the following reagents

| Post-Capture LM-PCR Master Mix | Per Individual DNA Sample PCR Reaction |
| --- | --- |
| KAPA HiFi HotStart ReadyMix (2X) | 25 μl |
| Post-LM-PCR Oligos 1 & 2, 5 μM* | 5 μl |
| Total | 30 μl |

4.2.2. Add 30 microliters Post-Capture LM-PCR Master Mix to 0.2 ml tube or well of PCR plate.

4.2.3. Mix thoroughly the bead-bound DNA from step 3.3.

4.2.4. Aliquot 20 microliters of bead-bound DNA as template into the tube/well with the 30 ul Post-capture LM-PCR Master Mix. (If performing a negative control, add 20 ul PCR-grade water to this tube/well).

4.2.5. Mix thoroughly by pipetting up and down several times.

4.3. Perform the Post-Capture PCR Amplification.

4.3.1. Place the sample in the thermocycler. It is recommended to set the heated lid of the thermocycler to track +10° C. above the incubation temperature during amplification steps.

4.3.2. Amplify the captured DNA using the following Post-Capture LM-PCR program:

4.3.2.1. Step 1: 45 seconds at +98° C.

4.3.2.2. Step 2: 15 seconds at +98° C.

4.3.2.3. Step 3: 30 seconds at +60° C.

4.3.2.4. Step 4: 30 seconds at +72° C.

4.3.2.5. Step 5: Go to Step 2, repeat 0 or 1 times (for a total of 1 or 2 cycles)

4.3.2.6. Step 6: 1 minutes at +72° C.

4.3.2.7. Step 7: Hold at +4° C.

4.3.2.8. Store reactions at +2 to +8° C. until ready for purification, up to 72 hours.

4.4. Purify the Amplified Captured DNA Sample using Agencourt AMPure XP Beads 4.4.1. Allow the AMPure XP Beads, contained in the SeqCap Pure Capture Bead Kit, to warm to room temperature for at least 30 minutes before use.

4.4.2. Vortex the AMPure XP beads for 10 seconds before use to ensure a homogenous mixture of beads.

4.4.3. Add 90 microliters AMPure XP Beads to the 50 microliters amplified captured DNA Sample library.

4.4.4. Mix thoroughly by vortexing or pipetting up and down multiple times.

4.4.5. Incubate at room temperature for 5 minutes to allow the captured sample library to bind to the beads.

4.4.6. Place the samples containing the bead-bound DNA on a magnetic particle collector to capture the beads. Allow the solution to clear.

4.4.7. Once clear, remove and discard the supernatant being careful not to disturb the beads.

4.4.8. Add 200 microliters freshly-prepared 80% ethanol to the samples containing the beads plus sample library. The samples should be left in the magnetic particle collector during this step.

4.4.9. Incubate at room temperature for ≥30 seconds.

4.4.10. Remove and discard the 80% ethanol.

4.4.11. Keeping the samples on the magnetic particle collector, add 200 microliters of freshly-prepared 80% ethanol.

4.4.12. Incubate the samples at room temperature for ≥30 seconds.

4.4.13. Carefully remove and discard the ethanol. Try to remove all residual ethanol without disturbing the beads.

4.4.14. Allow the beads to dry at room temperature with the tube lid open for 5 minutes (or until dry).

4.4.15. Remove the samples from the magnetic particle collector.

4.4.16. Resuspend the DNA using 53 microliters of 10 mM Tris-HCl, pH 8.0 or PCR-grade water.

4.4.17. Pipette up and down ten times to mix to ensure that all of the beads are resuspended.

4.4.18. Incubate at room temperature for 2 minutes.

4.4.19. Place the samples back on the magnetic particle collector and allow the solution to clear.

4.4.20. Remove 50 microliters of the supernatant that now contains the amplified captured DNA Sample Library Pool and transfer into a new tube/well.

4.5. Determine the Concentration, Size Distribution, and Quality of the Amplified Captured DNA Sample 4.5.1. Quantify the DNA concentration and measure the A260/A280 ratio of the amplified captured DNA and negative control.

4.5.1.1. The A260/A280 ratio should be 1.7-2.0.

4.5.1.2. The LM-PCR yield should be approximately 500 ng.

4.5.1.3. The negative control should not show significant amplification, which could be indicative of contamination.

4.5.2. Run 1 microliters of the amplified captured DNA sample and negative control using an Agilent Bioanalyzer DNA 1000 chip. Run the chip according to manufacturer's instructions. Amplified captured DNA should exhibit an average fragment length between 150-500 bp:

4.5.3. The amplified captured DNA is ready for sequencing.

Example 5—Sequence the Captured Sample Library 5.1. Sequence the amplified captured DNA using an Illumina sequencing instrument, according to manufacturer's instructions.

Example 6—Comparison of the Effect of the Number of Amplification Cycles on Targeted Sequencing Using the protocols set forth in Examples 1 through 5 herein, seven experiments were performed using the same amount of input genomic DNA (3 micrograms) obtained from the same source (cell line human genomic DNA, NA12891, Coriell Institutes). The biotinylated oligonucleotide probes used for the experiments targeted the exons of 578 genes implicated in cancer, with a cumulative capture target of 4,571,289 base pairs (Design ID: 120522_HG19_Onco_R_EZ, Roche NimbleGen, Inc.). No pre-capture PCR amplification was performed for any of the seven experiments, but the number of post-capture PCR amplification cycles was varied between 0 and 14 (0, 1, 2, 4, 6, 10, and 14).

Figure 5:
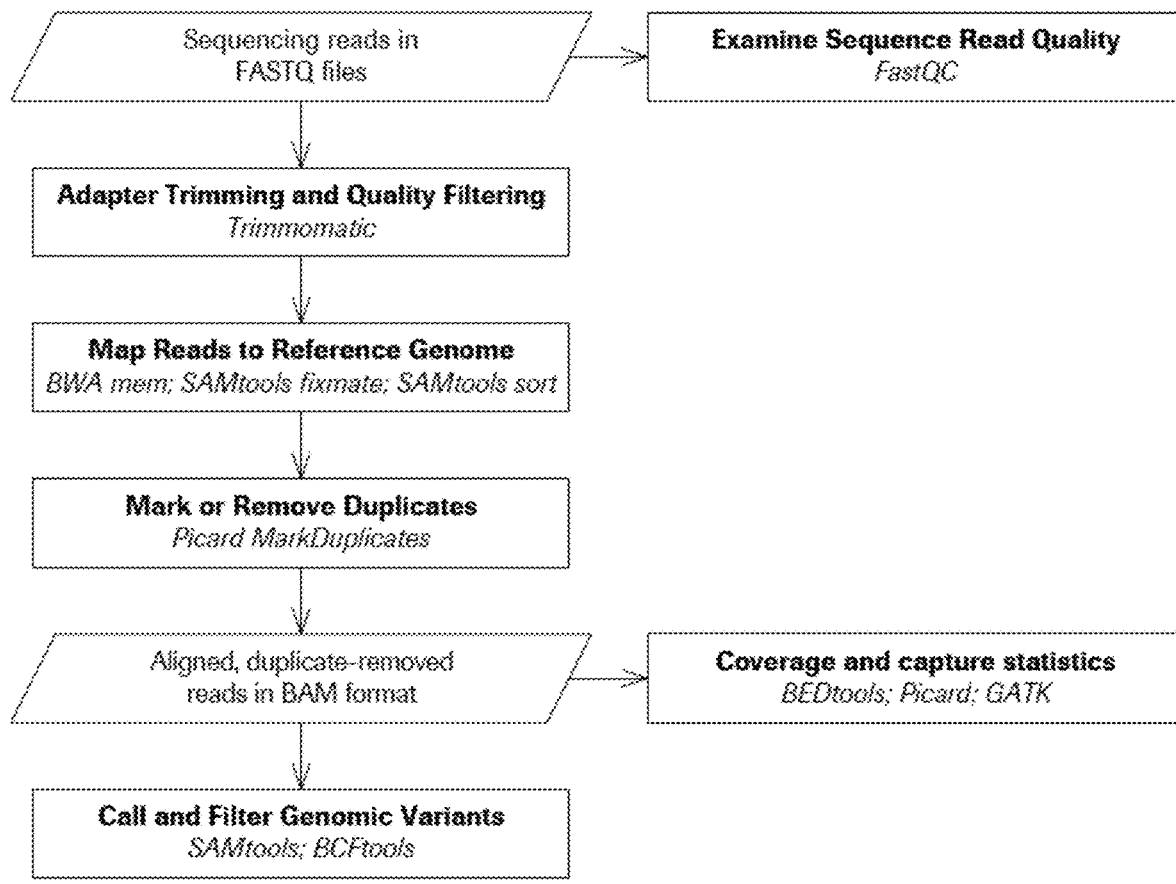
FIG. 5 displays a schematic of the basic SeqCap EZ sequence capture data analysis workflow. The sequencing reads from the sequence capture experiment are organized in the widely used "FASTQ" file format. Sequence read quality is evaluated using the program "FastQC" to determine if the data are of sufficient quality to continue analysis. Any sequencing adapters and poor quality reads are then filtered out using the program "Trimmomatic" to allow the remaining reads to be efficiently mapped to the reference genome using the program "BWA mem." The "SAMtools fixmate" program ensures consistent information appears for both reads in a pair. The "SAMtools sort" program is then used to order the output file according to genomic sort order. After mapping, the "Picard MarkDuplicates" command is used to remove or mark PCR duplicates to avoid allele amplification bias in variant calling. The mapped reads with amplification associated duplicates removed are then converted to the "BAM" format for subsequent analysis. Sequence coverage and capture statistics are generated using the programs "BEDtools," "Picard," and "GATK," while genomic sequence variants are called and filtered using "SAMtools" and "BCFtools." A detailed description of these methods is described in the Roche Technical Note document entitled "How to Evaluate NimbleGen SeqCap EZ Target Enrichment Data (August 25, the disclosure of which is hereby incorporated by reference herein in its entirety).
Figure 6:
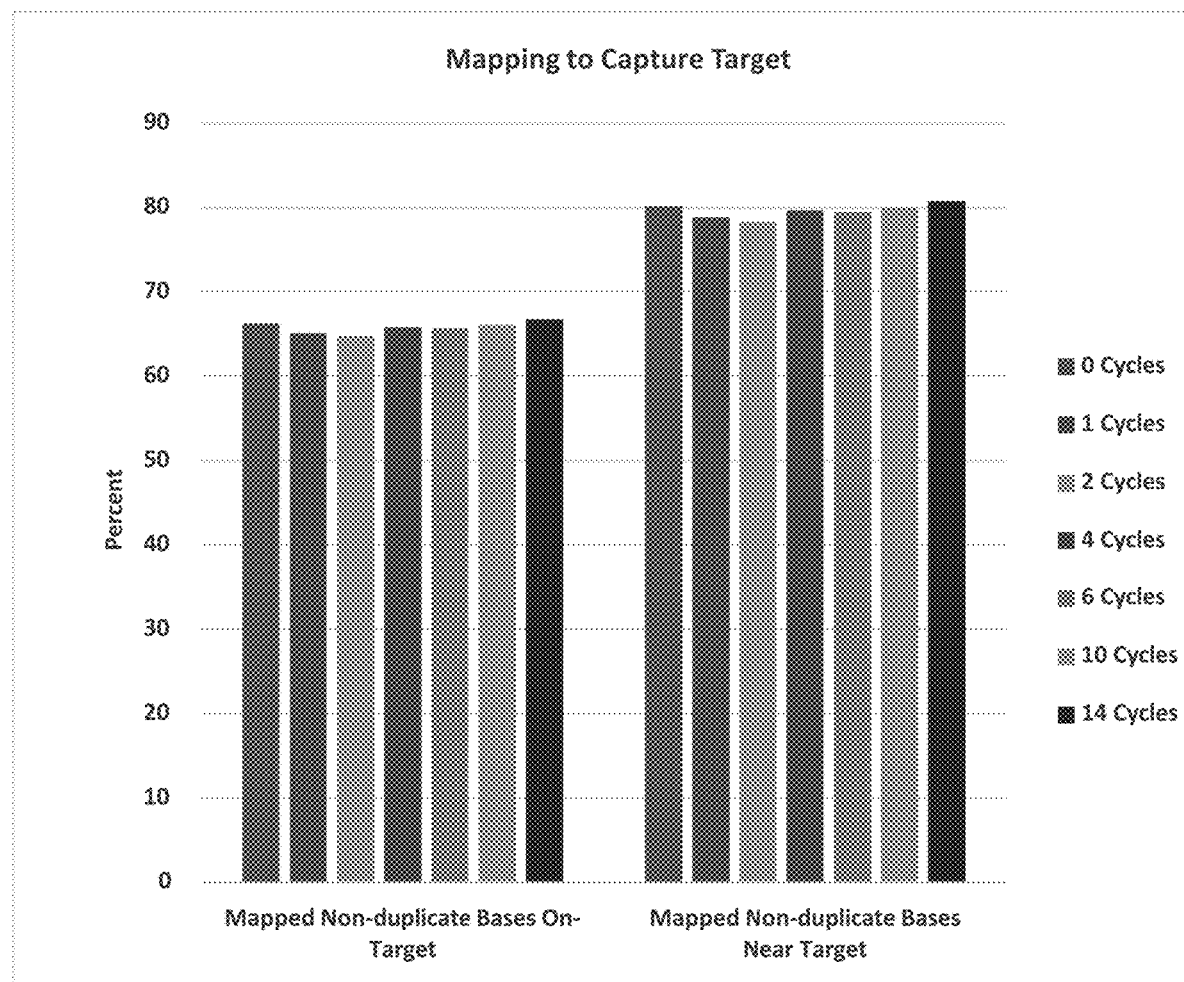
FIG. 6 shows that the percentage of all non-duplicate sequenced bases that map to the genome and align to the capture target ("On-target"), or are located within 100 base pairs of the capture target ("Near Target"), are not substantially different whether the experiment utilized 0, 1, 2, 4, 6, 10 or 14 cycles of post-capture amplification. None of the experiments shown included a pre-capture amplification step. Sequenced bases that are on-target or near-target are used to identify sequence variants in the capture experiment. A reduction in the percentage of on-target or near-target bases in an experiment would necessitate costly additional compensatory sequencing to achieve the same absolute amount of useful data for identifying sequence variants. The unexpected capability of the amplification-free capture protocol to maintain good on-target rates, compared to protocols specifying amplification, indicates that it will facilitate cost- and time-savings on the amplification steps without incurring cost increases for compensatory sequencing.
Figure 7:
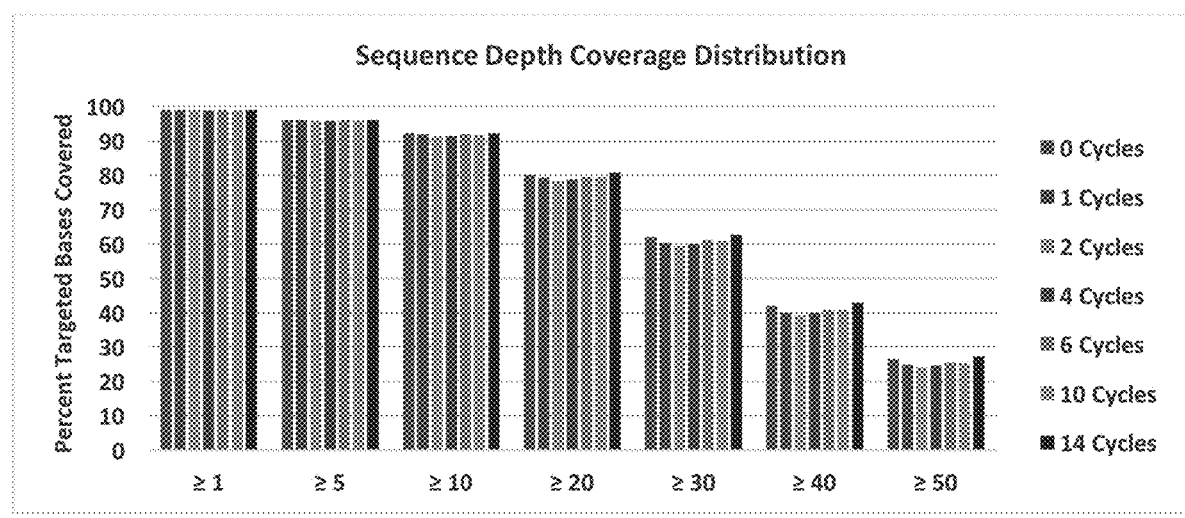
FIG. 7 shows that the percentage of all bases comprising the capture target that were covered with some minimum read depth ($\geq 1$, $\geq 5$, $\geq 10$, $\geq 20$, $\geq 30$, $\geq 40$, and $\geq 50$), were not substantially different whether the experiment utilized 0, 1, 2, 4, 6, 10 or 14 cycles of post-capture amplification. The sequence depth coverage distribution is a key determinant of the sensitivity of the assay to detect sequence variants throughout the entire capture target. Thus, the data indicate that the amplification-free capture protocol should have a sensitivity to detect sequence variants similar to capture protocols specifying amplification.
Figure 8:
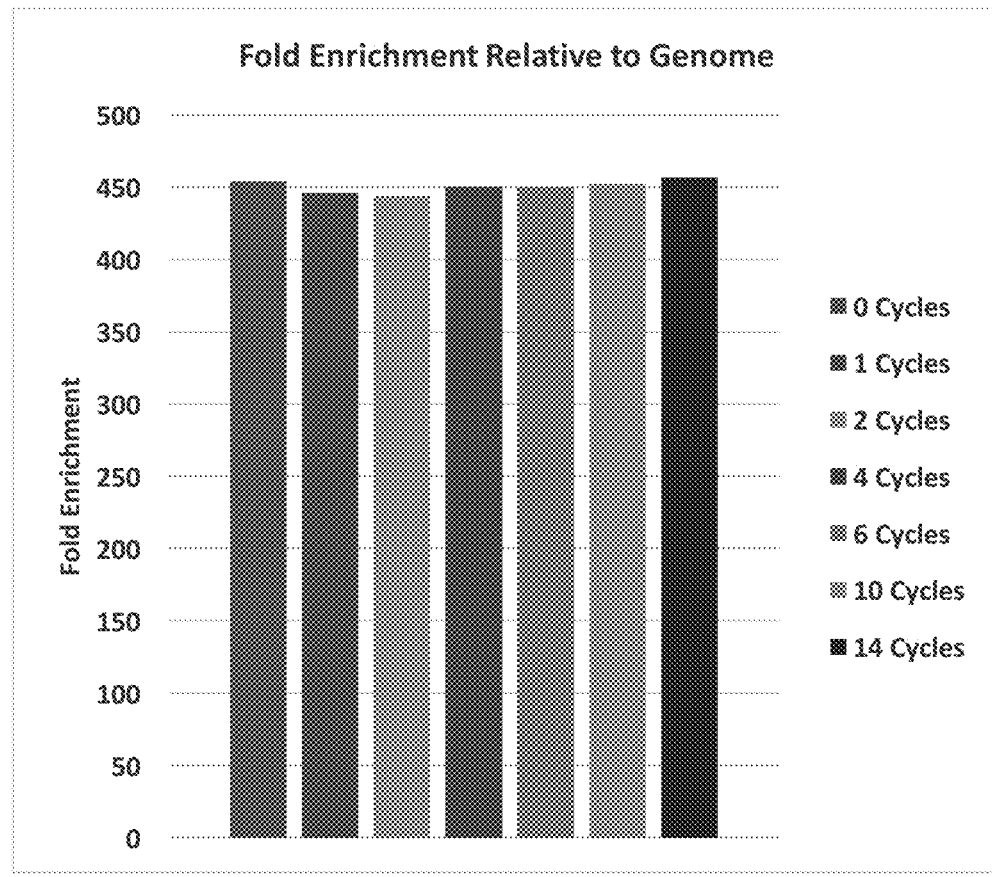
FIG. 8 show the fold enrichment of sequences in the capture target relative to the entire reference genome, calculated as the haploid genome size (~3,000,000,000 base pairs) divided by the capture target size (4,571,289 base pairs) multiplied by the percentage of sequenced bases that map within the capture target (mean of all seven experiments=0.667).
Figure 9:
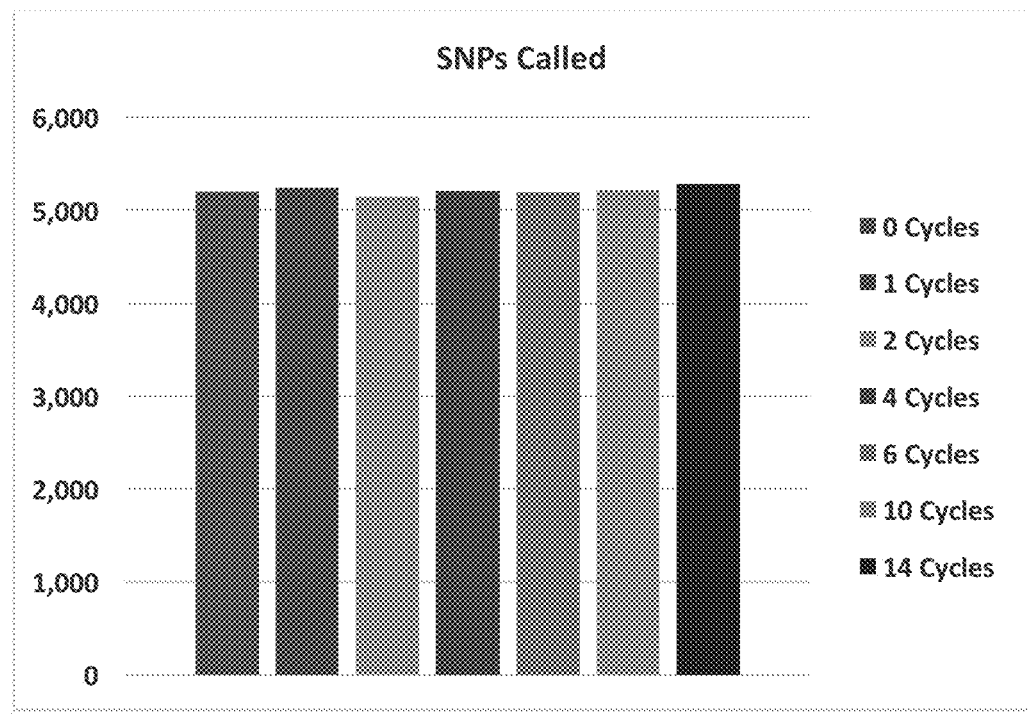
FIG. 9 shows the total number of single nucleotide polymorphisms (SNPs) called by the data analysis pipeline described in FIG. 5, relative to the sequence of the reference genome. The data indicate that the amplification-free capture protocol resulted in a similar number of SNPs called compared to the capture protocols specifying amplification.
Figure 10:
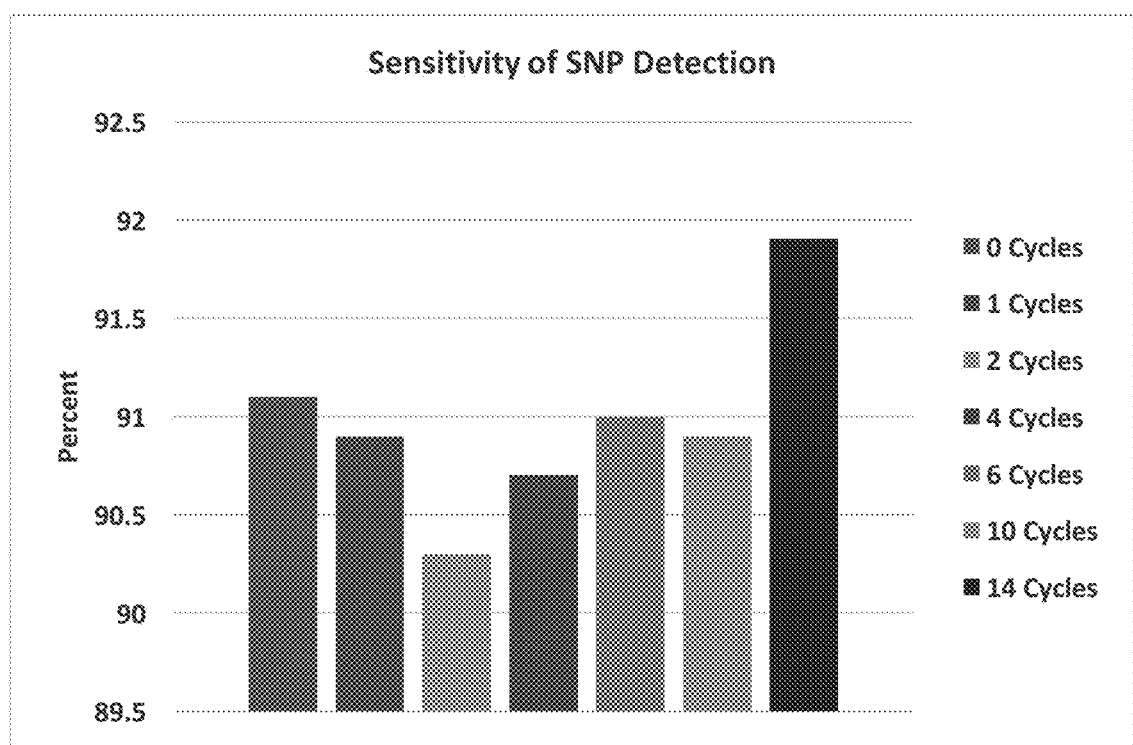
FIG. 10 shows the percentage of SNPs known to exist in the capture target of this particular DNA sample (NA1281, previously genotyped by the International HapMap Project) that were identified in the capture experiments we performed. Sensitivities ranging between 0.903-0.919 were calculated among all seven experiments, with the sensitivity of the PCR-free capture protocol calculated at 0.911, intermediate among the others.
Figure 11:
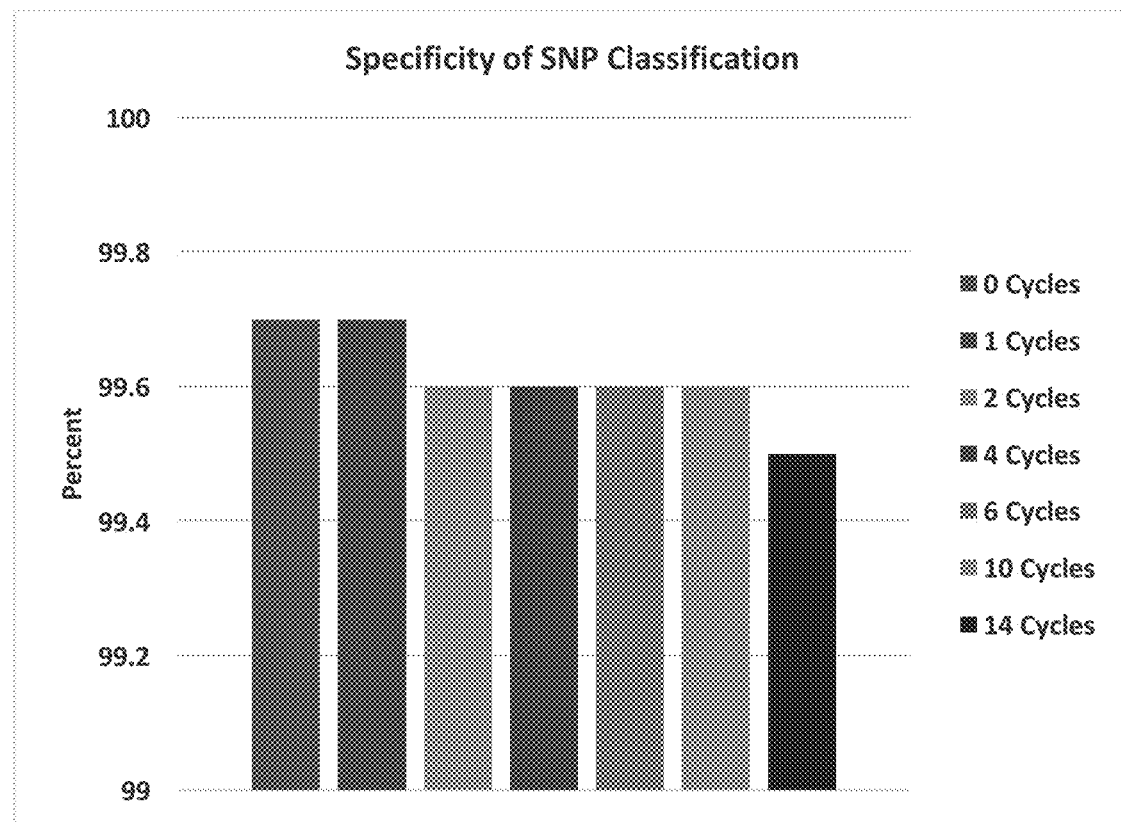
FIG. 11 shows the specificity of SNP classification in the seven capture experiments. For those known variants detected in the sample (NA12891), specificity of SNP classification is defined as the percentage that had the correct zygosity (homozygous versus heterozygous). A reduction in the specificity of SNP classification would be a predicted result of amplification-related allele bias (e.g. heterozygous genotypes might be more likely to appear as homozygous genotypes). The amplification-free capture protocol demonstrated a specificity of SNP classification similar to or greater than those capture protocols specifying amplification, consistent with the absence, by definition, of amplification-related allele bias.

The resulting amplified captured DNA was sequenced using an Illumina MiSeq sequencing instrument, with 2×100 paired-end sequencing, according to manufacturer's instructions. For each of the seven experiments, the resulting reads were randomly sampled to 1.75 million read pairs (3,500,000 reads) to facilitate comparison of the assay performance using equal amounts of data. Data analysis was performed using standard bioinformatic methods described in the Roche Technical Note document entitled "How to Evaluate NimbleGen SeqCap EZ Target Enrichment Data (August 2015, the disclosure of which is hereby incorporated by reference herein in its entirety). A schematic of the analysis workflow is shown in FIG. 5.

Experimental results are presented in FIGS. 6 to 11 for six frequently used targeted sequencing assay performance metrics. Values for the percentage of sequenced bases mapping to the capture target or near the capture target (FIG. 6), the distribution of sequence depth coverage over the capture target (FIG. 7), the fold enrichment of targeted sequences relative to the genome (FIG. 8), the total number of single nucleotide polymorphisms (SNPs) called (FIG. 9), the sensitivity of SNP detection (FIG. 10), and the specificity of SNP classification (FIG. 11), were similar among experiments that utilized 0, 1, 2, 4, 6, 10 or 14 cycles of PCR amplification. Current methods for targeted sequencing via hybridization to biotinylated oligonucleotide probes require the use of multiple cycles of PCR amplification within the workflow, and typically greater than 4 amplification cycles (see FIGS. 1 and 4). The results presented here unexpectedly demonstrate that the disclosed Targeted Representational Sequencing methods enable targeted sequencing to be performed with minimal or no amplification cycles, such as described herein, without incurring any striking reduction in assay performance.

STATEMENT OF INDUSTRIAL APPLICABILITY

The present disclosure has industrial applicability in the field of medicine and diagnostics.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

The invention claimed is:

1. A method of sequencing genomic material within at least one of tumor sample, a lymph node sample, or a blood sample comprising: (a) isolating between about 10 micrograms to about 250 micrograms of the genomic material from the at least one of the tumor sample, the lymph node sample, or the blood sample wherein the isolating of the genomic material comprises: (i) homogenizing the at least one of the tumor sample, the lymph node sample, or the blood sample to provide a homogenized sample, wherein any heterogeneity of cells within the at least one of the tumor sample, the lymph node, or the blood sample is substantially uniformly distributed within the at least the portion of the homogenized sample; (ii) lysing the cellular components within the homogenized sample to provide a lysed homogenized sample; and (iii) extracting genomic material from the lysed homogenized sample, wherein the extracted genomic material is representative of the nucleic acids present within the at least one of the tumor sample, the lymph node sample, or the blood sample, and wherein the extracted genomic material comprises target and non-target nucleic acid molecules; (b) enriching the extracted genomic material for target nucleic acid molecules, wherein the enriching provides between about 90 ng and about 900 ng of enriched genomic material; and (c) sequencing the enriched genomic material without performing post-capture amplification; and wherein no pre-capture amplification cycles are conducted prior to the sequencing of the captured genomic material.

2. The method of claim 1, wherein between about 50 micrograms and about 100 micrograms of genomic material are isolated from the at least one of the tumor sample, the lymph node sample, or the blood sample.

3. A method of targeted representational sequencing comprising: (i) disassociating at least a portion of a tumor, one or more whole or partial lymph nodes, or any combination thereof to provide a homogenized sample, wherein any subpopulations of tumor cells that were originally spatially segregated within the tumor and/or the one or more whole or partial lymph nodes are distributed throughout the homogenized sample; (ii) lysing the cellular components within the homogenized sample to provide a lysed homogenized sample; (iii) extracting between about 10 micrograms to about 100 micrograms of genomic material from the —lysed homogenized sample, wherein the extracted genomic material comprises target and non-target nucleic acid molecules; (iv) enriching the extracted genomic material for target nucleic acid molecules to provide between about 90 ng to about 900 ng of enriched genomic material; and (v) sequencing the enriched genomic material without performing post-capture amplification, wherein no pre-capture amplification cycles are conducted prior to the sequencing of the captured genomic material.

4. A method of reducing PCR-introduced mutations during sequencing comprising: isolating between about 10 micrograms to about 100 micrograms of DNA from a homogenized sample, wherein the homogenized sample substantially expresses a heterogeneity of cells of a tumor sample or lymph node sample from which the homogenized sample was derived; enriching the isolated DNA for target nucleic acid molecules, wherein an amount of enriched isolated DNA ranges from between about 90 ng to about 900 ng; and sequencing the enriched isolated DNA without performing post-capture amplification, and wherein no pre-capture amplification cycles are performed on the prepared isolated DNA prior to sequencing.

5. The method of claim 4, wherein the sample is derived from a patient suspected of having cancer.

6. The method of claim 4, wherein the sample is derived from a patient diagnosed with cancer.

7. The method of claim 4, wherein the sample is derived from a patient at risk of developing cancer.

8. The method of claim 4, wherein the sample is derived from healthy tissue samples.

9. The method of claim 1, wherein the sample comprises at least 1,500,000 cells.

10. The method of claim 3, wherein the sample comprises at least 1,500,000 cells.

11. The method of claim 4, wherein the sample comprises at least 1,500,000 cells.

12. The method of claim 1, wherein the enriching of the extracted genomic material for target nucleic acid molecules comprises: (i) hybridizing the extracted genomic material to probes to capture the target nucleic acid molecules within the extracted genomic material; (ii) removing non-target nucleic acids; and (iii) releasing the enriched extracted genomic material from the probes.

13. The method of claim 1, wherein the homogenization comprises mechanical shearing.

14. The method of claim 1, wherein the sequencing comprises next generation sequencing.

15. The method of claim 3, wherein the enriching of the extracted genomic material for target nucleic acid molecules comprises: (i) hybridizing the extracted genomic material to probes to capture the target nucleic acid molecules within the extracted genomic material; (ii) removing non-target nucleic acids; and (iii) releasing the enriched extracted genomic material from the probes.

16. The method of claim 3, wherein the dissociation comprises mechanical shearing.

17. The method of claim 3, wherein the sequencing comprises next generation sequencing.

18. The method of claim 4, wherein the enriching of the isolated DNA for target nucleic acid molecules comprises: (i) hybridizing the extracted genomic material to probes to capture the target nucleic acid molecules within the extracted genomic material;
(ii) removing non-target nucleic acids; and (iii) releasing the enriched isolated DNA from the probes.

19. The method of claim 4, wherein the sequencing comprises next generation sequencing.

* * * * *